US008940508B2

(12) United States Patent
Peers

(10) Patent No.: US 8,940,508 B2
(45) Date of Patent: Jan. 27, 2015

(54) ENHANCEMENT OF BIOMASS PRODUCTION BY DISRUPTION OF LIGHT ENERGY DISSIPATION PATHWAYS

(75) Inventor: Graham Peers, Fort Collins, CO (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/332,101

(22) Filed: Dec. 20, 2011

(65) Prior Publication Data
US 2012/0178134 A1 Jul. 12, 2012

Related U.S. Application Data

(60) Provisional application No. 61/428,876, filed on Dec. 31, 2010.

(51) Int. Cl.
*C12P 7/64* (2006.01)
*C12N 13/00* (2006.01)
*C07K 14/195* (2006.01)
*C12N 1/12* (2006.01)

(52) U.S. Cl.
CPC .............. *C12N 13/00* (2013.01); *C07K 14/195* (2013.01); *C12P 7/6409* (2013.01); *C12P 7/6463* (2013.01); *C12N 1/12* (2013.01)
USPC ....................................... 435/134

(58) Field of Classification Search
CPC ..... C12P 7/6472; C12P 7/6427; C12P 7/6463
USPC ....................................... 435/134
See application file for complete search history.

(56) References Cited

U.S. PATENT DOCUMENTS

| | | | |
|---|---|---|---|
| 5,447,858 A | 9/1995 | Key et al. | 435/172.3 |
| 5,455,167 A | 10/1995 | Voelker et al. | 435/172.3 |
| 5,639,952 A | 6/1997 | Quail et al. | 800/205 |
| 5,654,495 A | 8/1997 | Voelker et al. | 800/250 |
| 5,661,017 A | 8/1997 | Dunahay et al. | 435/172.3 |
| 5,689,044 A | 11/1997 | Ryals et al. | 800/205 |
| 5,750,385 A | 5/1998 | Shewmaker et al. | 435/172.3 |
| 5,851,796 A | 12/1998 | Schatz | 435/69.1 |
| 6,379,945 B1 | 4/2002 | Jepson et al. | 435/243 |
| 6,410,828 B1 | 6/2002 | Armstrong et al. | 800/287 |
| 7,135,290 B2 | 11/2006 | Dillon | 435/6 |
| 7,294,506 B2 | 11/2007 | Daniell et al. | 435/320.1 |
| 2009/0011492 A1 | 1/2009 | Berzin | 435/257.1 |
| 2010/0251601 A1 | 10/2010 | Hu et al. | 44/313 |
| 2010/0285105 A1 | 11/2010 | Radianingtyas et al. | 424/450 |
| 2010/0297736 A1 | 11/2010 | Duhring et al. | 435/252.3 |

FOREIGN PATENT DOCUMENTS

| | | | | |
|---|---|---|---|---|
| WO | WO 00/62601 | 10/2000 | ............ | A01H 13/00 |
| WO | WO 03/091413 | 11/2003 | | |
| WO | WO 2005/005643 | 1/2005 | ............ | C12N 15/82 |
| WO | WO 2007/133558 | 11/2007 | ............ | E21B 37/00 |
| WO | WO 2008119082 A2 * | 10/2008 | | |
| WO | WO 2010/075483 | 7/2010 | ............... | C12N 9/16 |
| WO | WO 2011/143619 | 11/2011 | ............... | C12M 1/00 |

OTHER PUBLICATIONS

Beckmann, J et al. Improvement of light to biomass conversion by de-regulation of light-harvesting protein translation in Chlamydomonas reinhardtii. 2009. Journal of Bacteriology. 142:70-77.*

Beckmann, J et al. Improvement of light to biomass conversion by de-regulation of light-harvesting protein translation in Chlamydomonas reinhardtii. 2009. Journal of Biotechnology. 142:70-77.*

Abe, J., et al. (2008), "Expression of exogenous genes under the control of endogenous HSP70 and CAB promoters in the *Closterium peracerosum-strigosum-littorale* complex", *Plant Cell Physiol*, 49(4): 625-632.

Altschul, S., et al., (1997), "Gapped Blast and PSI-Blast: a new generation of protein database search programs", *Nucleic Acids Research*, 25(17): 3389-3402.

Bateman, A., et al. (2000), "The pfam protein families database", *Nucleic Acids Research*, 28(1):263-266.

Bateman, A., et al. (2004), "The pfam protein families database", *Nucleic Acids Research*, 32: Database Issue: D138-D141.

Ben-Amotz, A., et al. (1995) "New mode of *Dunaliella* biotechnology: two-phase growth for β-carotene production", *Journal of Applied Phycology*, 7: 65-68.

Boulay, C., et al., (2008) "Occurrence and function of the orange carotenoid protein in photoprotective mechanisms in various cyanobacteria" *Biochim Biophys Acta*, 1777(10): 1344-1354.

Boulay, C., et al., (2010), "Identification of a protein required for recovery of full antenna capacity in OCP-Related photoprotective mechanism in cyanobacteria", PNAS, 107(25): 11620-11625.

(Continued)

*Primary Examiner* — David J Steadman
*Assistant Examiner* — Paul Holland
(74) *Attorney, Agent, or Firm* — Harness, Dickey & Pierce, P.L.C.

(57) ABSTRACT

The invention provides a method of producing biomass or at least one biomolecule comprising culturing a photosynthetic microorganism that comprises a disrupted Non-Photochemical Quenching (NPQ) process, and isolating biomass or at least one biomolecule from the culture.

17 Claims, 3 Drawing Sheets

(56) References Cited

OTHER PUBLICATIONS

Brunet, C., et al., (2010), "Can the xanthophyll cycle help extract the essence of the mircoalgal functional response to a variable light environment?", *Journal of Plankton Research*, 32(12): 1609-1617.

Buikema, W., et al. (2000), "Expression of the anabaena hetR gene from a copper-regulated promoter leads to heterocyst differentiation under repressing conditions", *Proc. Natl. Acad. Sciences USA* 98(5): 2729-2734.

Chàbera, P., et al. (2011), "Excited-state properties of the 16 kDa red carotenoid protein from *Arthrospira maxima*" *Biochim Biophys Acta*, 1807: 30-35.

Degen, J., et al. (2001), "A novel airlift photobioreactor with baffles for improved light utilization through the flashing light effect", *Journal of Biotechnology*, 92: 89-94.

Demmig-Adams, B., et al. (1996) "In vivo functions of carotenoids in higher plants" *FASEB J.* 10: 403-412.

El Bissati, K., et al. (2000), "Photosystem II fluorescence quenching in the cyanobacterium *Synechocystis* PCC 6803: involvement of two different mechanisms", *Biochim Biophys Acta*, 1457: 229-242.

Finn, R., et al. (2006), "Pfam: clans, web tools and services", *Nucleic Acids Research*, 34: Database Issue 34:D247-D251.

Finn, R., et al. (2010), "The pham protein families database", *Nucleic Acids Research*, 38: Database Issue 38:D211-D222.

Gwizdala, M., et al. (2011), "In vitro reconstitution of the cyanobacterial photoprotective mechanism mediated by the orange carotenoid protein in *Synechocystis* PCC 6803", *The Plant Cell*, 23: 2631-2643.

Hallmann, A., et al. (1997), "Gene replacement by homologous recombination in the multicellular green alga *Volvox carteri*" *Proc. Natl. Acad. Sci USA*, 94:7469-7474.

Heger, A., et al., (2003) "Exhaustive enumeration of protein domain families" *J. Mol. Biol.*, 328: 749-767.

Henikoff, S., et al. (1992), "Amino acid substitution matrices from protein blocks", *Proc. Natl. Acad. Sci USA*, 89:10915-10919.

International Search Report for PCT/US11/66241 mailed on May 3, 2012.

Iwai, M., et al. (2004), "Improved genetic transformation of the thermophilic cyanobacterium, thermosynechoccus elongates BP-1", *Plant Cell Physiol.* 45(2):171-175.

Karlin, S., et al., (1990), "Methods for assessing the statistical significance of molecular sequence features by using general scoring schemes", *Proc. Natl. Acad. Sci. USA*, 87: 2264-2268.

Kirliovsky, D., et al. (2007), "Photoprotection in cyanobacteria: the orange carotenoid protein (OCP)-related non-photochemical-quenching mechanism", *Photosynth Res* 93:7-16.

Kindle, K., et al. (1989), "Stable nuclear transformation of *Chlamydomonas* using the *Chlamydomonas* gene for nitrate reductase", *The Journal of Cell Biology*, 109 (6, Part 1), 2589-2601.

Lehr, F., et a., (2009) "Closed photo-bioreactors as tools for biofuel production", *Curr Opinion Biotechnol*, 20: 280-285.

Lee, M., et al. (2006) "Isolation and characterization of a xanthophyll aberrant mutant of the green alga *Nannochloropsis oculata*", *Marine Biotechnology* 8: 238-245.

Liu, X., et al. (2009), "Nickel-inducible lysis system in *synechocystis* sp. *PCC 6803*", *Proc. Natl. Acad. Sciences USA* 106: 21550-21554.

Méndez-Alvarez, S., et al. (1994), "Transformation of *Chlorobium limicola* by a plasmid that confers the ability to utilize thiosulfate" *Journal of Bacteriology*,176(23):7395-7397.

Mochimaru, M., et al. (2005), "The cyanobacterium *Anabaena* sp. *PCC 7120* has two distinct β-carotene ketolases: CrtO for echinemone and CrtW for ketomyxol synthesis", *FEBS Letters*, 579: 6111-6114.

Ohnuma M., et al. (2008), "Polyethylene glycol (PEG)-mediated transient gene expression in a red alga, *Cyanidioschyzon merolae* 10D", *Plant Cell Physiol.* 49(1):117-120.

Olaizola, M., (2000) "Commercial production of astaxanthin from *Haematococcus pluvialis* using 25,000—liter outdoor photobioreactors" *Journal of Applied Phycology* 12(3): 499-506.

Park, K., et al. (2001), "Effectiveness of flashing light for increasing photosynthetic efficiency of microalgal cultures over a critical cell density", *Biotechnol. Bioprocess Eng.* 6: 189-193.

Peers, G., et al. (2009), "An ancient light-harvesting protein is critical for the regulation of algal photosynthesis", *Nature*, 462: 518-522.

Perrone, C., et al. (1998), "The *Chlamydomonas* IDA7 locus encodes a 140 kDa dynein intermediate chain required to assemble the I1 inner arm complex", *Molecular biology of the Cell*, 9:3351-3365.

Punginelli, C., et al. (2009), "Influence of zeaxanthin and echineone binding on the activity of the orange carotenoid protein", *Biochimica et Biophysica Acta*, 208-288.

Ramesh, V., et al. (2004), "A simple method for chloroplast transformation in *Chlamydomonas reinhardtii*" *Methods in Molecular Biology*, 274:301-307.

Ravindran, C., et al. (2006), "Electroporation as a tool to transfer the plasmid pRL489 in *Oscillatoria* MKU 277" *Journal of Microbiological Methods*, 66:174-176.

Schroda, M., et al. (2000), "The HSP70A promoter as a tool for improved expression of transgenes in *Chlamydomonas*", *The plant journal* 21(2):121-131.

Sonnhammer, E., et al. (1998), "Pfam: multiple sequence alignments and HMM-profiles of protein domains" *Nucleic Acids Research* 26(1):320-322.

Steinbrenner, J., et al. (2006), "Transformation of the Green Alga *Haematococcus pluvialis* with a phytoene Desaturase for accelerated astaxanthin biosynthesis" *Applied and Environmental Microbiology* 72(I2):7477-7484.

Sun, Y., et al. (2006), "Functional complementation of a nitrate reductase defective mutant of a green alga *Dunaliella viridis* by introducing the nitrate reductase gene", *Gene* 377:140-149.

Tan, C., et al. (2005), "Establishment of a micro-particle bombardment transformation system for *Dunaliella salina*", *The Journal of Microbiology*, 43:361-365.

Van Kooten, O., et al. (1990), "The use of cholorphyll fluorescence nomenclature in plant stress physiology", *Photosynth Res*, 25: 147-150.

Wilson, A., et al., (2006) "A soluble carotenoid protein involved in phycobilisome-related energy dissipation in cyanobacteria", *The Plant Cell* 18: 992-1007.

Wilson, A., et al. (2007) "Light-induced energy dissipation in iron-starved cyanobacteria: roles of OCP and IsiA proteins" *The Plant Cell* 19:656-672.

Wilson, A., et al. (2008) "A photoactive carotenoid protein acting as light intensity sensor" *Proc. Natl. Acad. Sci. USA*, 105(33):12075-12080.

Wilson, A., et al. (2010) "Structural determinants underlying photoprotection in the photoactive orange carotenoid protein of cyanobacteria" *J. Biol. Chem.* 285(24):18364-18375.

Xu, L., et al., (2009) "Microalgal bioreactors: challenges and opportunities", *Eng. Life Sci*, 9(3): 178-189.

Karapetyan, N. V. (2007) "Non-photochemical quenching of fluorescence in cyanobacteria", *Biochemistry*, 72(10):1127-1135.

Ort, D.R., et al. (2011) "Optimizing antenna size to maximize photosynthetic efficiency", *Plant Physiology*, 155:79-85.

Polle, J.E.W. et al. (2003) "tla1, a DNA insertional transformant of the green alga *Chlamydomonas reinhardtii* with a truncated light-harvesting chlorophyll antenna size", *Planta*, 217:49-59.

Supplementary European Search Report dated Apr. 10, 2014 issued in European Application No. EP 11 85 4136.

* cited by examiner

SEQUENCE LISTING

<160> NUMBER OF SEQ ID NOS: 24

<210> SEQ ID NO 1
<211> LENGTH: 954
<212> TYPE: DNA
<213> ORGANISM: Synechocystis PCC6803

<400> SEQUENCE: 1

```
atgccattca ccattgactc tgcccgcgga attttcccta acaccctagc ggccgacgtt      60
gtacccgcta ccatcgcccg ttttagccaa ctcaatgccg aagatcaatt agctctgatt     120
tggtttgctt acctagaaat gggtaaaacc cttacgatcg ccgcccctgg ggccgccagc     180
atgcaactgg ccgaaaatgc cctcaaggaa attcaagcca tggggcccct ccaacaaacc     240
caggccatgt gtgacttggc caaccgagct gacactcccc tgtgccgcac ctacgccagt     300
tggtccccca acattaaact tggcttctgg taccgtttag gcgaactgat ggagcagggc     360
tttgtcgccc ccattcccgc tggttaccaa ctttctgcca atgccaatgc agtgctagct     420
acgatccaag gcctagaatc cggtcaacaa attaccgtat tgcgtaatgc cgtggtggac     480
atgggcttca ccgctggtaa ggacggcaaa cgcatcgctg agcccgtagt tcctcccaa      540 gataccgcca gccgcaccaa agtttccatt gaaggggtga ccaatgccac tgtcctcaac     600
tacatggaca acctcaatgc caatgacttc gacaccttaa tcgaattgtt cacctccgac     660
ggtgccctcc aaccgccctt ccaacggccc attgtcggta agaaaatgt gctccgcttt      720 ttccgggaag agtgccaaaa cctgaaattg atcccggaac gggggttac tgaacccgct     780 gaagatggtt tcacccaaat taaagttacc ggtaaggtgc aaaccccttg gtttggtggc     840
aacgtgggca tgaatatcgc ctggcgcttt ctcctcaacc ccgagggcaa aattttcttt     900
gtggcgatcg acctccttgc ttcccccaaa gaattactca actttgctcg ctag            954
```

<210> SEQ ID NO 2
<211> LENGTH: 317
<212> TYPE: PRT
<213> ORGANISM: Synechocystis PCC6803

<400> SEQUENCE: 2

Met Pro Phe Thr Ile Asp Ser Ala Arg Gly Ile Phe Pro Asn Thr Leu

```
            1               5                  10                 15
          Ala Ala Asp Val Val Pro Ala Thr Ile Ala Arg Phe Ser Gln Leu Asn
                          20                 25                 30

Ala Glu Asp Gln Leu Ala Leu Ile Trp Phe Ala Tyr Leu Glu Met Gly
                          35                 40                 45

Lys Thr Leu Thr Ile Ala Ala Pro Gly Ala Ala Ser Met Gln Leu Ala
                          50                 55                 60

Glu Asn Ala Leu Lys Glu Ile Gln Ala Met Gly Pro Leu Gln Gln Thr
          65                        70                 75                 80

Gln Ala Met Cys Asp Leu Ala Asn Arg Ala Asp Thr Pro Leu Cys Arg
                          85                 90                 95

Thr Tyr Ala Ser Trp Ser Pro Asn Ile Lys Leu Gly Phe Trp Tyr Arg
                          100                105                110

Leu Gly Glu Leu Met Glu Gln Gly Phe Val Ala Pro Ile Pro Ala Gly
                          115                120                125

Tyr Gln Leu Ser Ala Asn Ala Asn Ala Val Leu Ala Thr Ile Gln Gly
                          130                135                140

Leu Glu Ser Gly Gln Gln Ile Thr Val Leu Arg Asn Ala Val Val Asp
          145                       150                155                160

Met Gly Phe Thr Ala Gly Lys Asp Gly Lys Arg Ile Ala Glu Pro Val
                          165                170                175

Val Pro Pro Gln Asp Thr Ala Ser Arg Thr Lys Val Ser Ile Glu Gly
                          180                185                190

Val Thr Asn Ala Thr Val Leu Asn Tyr Met Asp Asn Leu Asn Ala Asn
                          195                200                205

Asp Phe Asp Thr Leu Ile Glu Leu Phe Thr Ser Asp Gly Ala Leu Gln
                          210                215                220

Pro Pro Phe Gln Arg Pro Ile Val Gly Lys Glu Asn Val Leu Arg Phe
          225                       230                235                240

Phe Arg Glu Glu Cys Gln Asn Leu Lys Leu Ile Pro Glu Arg Gly Val
                          245                250                255

Thr Glu Pro Ala Glu Asp Gly Phe Thr Gln Ile Lys Val Thr Gly Lys
                          260                265                270

Val Gln Thr Pro Trp Phe Gly Gly Asn Val Gly Met Asn Ile Ala Trp
                          275                280                285

Arg Phe Leu Leu Asn Pro Glu Gly Lys Ile Phe Phe Val Ala Ile Asp
                          290                295                300

Leu Leu Ala Ser Pro Lys Glu Leu Leu Asn Phe Ala Arg
          305                       310                315

<210> SEQ ID NO 3
<211> LENGTH: 5902
<212> TYPE: DNA
<213> ORGANISM: Artificial sequence
<220> FEATURE:
<223> OTHER INFORMATION: Construct for OCP Knock Out

<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
```

```
tacgccagct ggcgaaaggg ggatgtgctg caaggcgatt aagttgggta acgccagggt    360
tttcccagtc acgacgttgt aaaacgacgg ccagtgaatt cgagctcggt acccgtgcgg    420
agatagtaaa tgggagtatc ttcccttttgg ggaataatat ctttgagtag gggatgggcc    480
atggaatctt tctgaatgga gggaaacttt tccttagtag ctgtgttcag ataggtcaag    540
ttgccgaagt aatcgatctc caccatgggg tagggactat attcaataca ggcggctagt    600
ttagatagct tttcatggct cagttgggat aagtcatcct cgtggccaat cagagtgatg    660
tcccattgtt cctggggaaa atgctctgat agatctgggg ttaaccgctg gcgatcgccg    720
ccgccggaga tagtatcttt ggggtcggtg gggatggcct gatagaaaat ttgaatatct    780
tccgataggg cgatgacgtc tccatgcacc aactcataat ctagatggga ttcaccgtta    840
acccacactc cattacgact gcgatgacct tctaaatctc catcaatgat gtggaaggag    900
atatctaaat taggattaat tttttttgatt agggtggcgt ggcgacggga aatttgggga    960
gaaggaataa caatggtgtt gctcggatga cggccaatgg aataacaaga attttgtaaa   1020
cgaatgacct ttttaaacga gggtgaatca acgaccaatt gataaagcat aggagcgtta   1080
caggaaaaaa gctgagcctg aagaaaaata gttttagaga gtgactattg tcgcgactag   1140
ggaacaatta ttgatcacca ctccaaccag ttaccactga gaggaaataa ataatagaac   1200
aatctgattt gtatccgttg atgccatcat ttagattccc caactaatag tagcccacac   1260
aataattatt cagccactat attctttgtc ctattattgt caagctagga caaacttta    1320 gaaaaaatct gggttttcat tcggttttcc gatcctaaag ggggctacca aaccatggta   1380
aattctgggg aaagttgatt cacgtataaa acctggaaag ccacgttgtg tctcaaaatc   1440
tctgatgtta cattgcacaa gataaaaata tatcatcatg aacaataaaa ctgtctgctt   1500
acataaacag taatacaagg ggtgttatga gccatattca acgggaaacg tcttgctcga   1560
ggccgcgatt aaattccaac atggatgctg atttatatgg gtataaatgg gctcgcgata   1620
atgtcgggca atcaggtgcg acaatctatc gattgtatgg gaagcccgat gcgccagagt   1680
tgtttctgaa acatggcaaa ggtagcgttg ccaatgatgt tacagatgag atggtcagac   1740
taaactggct gacggaattt atgcctcttc cgaccatcaa gcattttatc cgtactcctg   1800
atgatgcatg gttactcacc actgcgatcc ccgggaaaac agcattccag gtattagaag   1860
aatatcctga ttcaggtgaa atattgttg atgcgctggc agtgttcctg cgccggttgc   1920
attcgattcc tgtttgtaat tgtccttta acagcgatcg cgtatttcgt ctcgctcagg   1980
cgcaatcacg aatgaataac ggtttggttg atgcgagtga ttttgatgac gagcgtaatg   2040
gctggcctgt tgaacaagtc tggaaagaaa tgcataagct tttgccattc tcaccggatt   2100
cagtcgtcac tcatggtgat ttctcacttg ataaccttat ttttgacgag gggaaattaa   2160
taggttgtat tgatgttgga cgagtcggaa tcgcagaccg ataccaggat cttgccatcc   2220
tatggaactg cctcggtgag ttttctcctt cattacagaa acggcttttt caaaaatatg   2280
gtattgataa tcctgatatg aataaattgc agtttcattt gatgctcgat gagttttct    2340 aatcagaatt ggttaattgg ttgtaacact ggcagagcat tacgctgact tgacgggacg   2400
gcggctttgt tgaataaatc gaactttttgc tgagttgaag gatcagatca cgcatcttcc   2460
cgacaacgca gaccgttccg tggcaaagca aaagttcaaa atcaccaact ggtccaccta   2520
caacaaagct ctcatcaacc gtggctcccct cactttctgg ctggatgatg gggcgattca   2580
ggcctggtat gagtcagcaa caccttcttc acgaggcaga cctcagcgcc aataactccc   2640
ttcagagttt tgtctttgcc atagtcggtc ggacaagcag ccaaaatact aataactgtg   2700
```

```
ggcttctcgt tgcagagcag gctcactttt tttattatgg taatgataat tacaaatcaa   2760
tatcataagt taatgttaca aaccgccgaa gcaccttggt cccaagctga aacccagtct   2820
gcccatgccc tgttccgtaa ggcctaccaa agagaattgg atggactgtt ggcaacggtg   2880
caagcccaag cttcccaaat tacgcagatc gatgatcttt ggaaactcca tgatttttg    2940 agtgcaaaac gccacgaaat tgatggcaag tacgacgatc gccagtcggt gattattttt   3000 gttttgccc aactgctcaa ggaaggtctg gtgcaagcgg aggaattgac ttttttagcc    3060
gccgataagc aatctaaaat taaggccctg gcccggctgt gattctagta aatatctaaa   3120
actccacaac tatgttcctg gggggaaatg gaattcatct gttagtcatt tctccgctgc   3180
cttgcttgct gtaggtgtac accgtttggg gctgccattg gtttagggcg tcggcggtga   3240
ggtcggcaaa ggatacattt tcccggtcca gactgacttg gagagtttcc atggggtctt   3300
tcccttgggc gatgaggaat gctagagcct gtaggtctgg ccattgtttg agctgtacga   3360
gaaaatcctt taccaaagcg gggtagggag aatggtcgtg cttttgccaa ggctggcccg   3420
atggtaagtt ttggtctagg ccgacgtgga aaattaggct attttgcca aatagggcga    3480 tcgccacggg gcggttgtct tcatgcacca tgaggggggt tccctgtaac agggcccgga   3540
ttttttccaa tttttcgtac cgttgttggg ccgaagcaac gttgggagta aatttaatgg    3600
cgatcgccag cagatagttt ttgactaacc ggggatcctc tagagtcgac ctgcaggcat   3660
gcaagcttgg cgtaatcatg gtcatagctg tttcctgtgt gaaattgtta tccgctcaca   3720
attccacaca acatacgagc cggaagcata aagtgtaaag cctggggtgc ctaatgagtg   3780
agctaactca cattaattgc gttgcgctca ctgcccgctt tccagtcggg aaacctgtcg   3840
tgccagctgc attaatgaat cggccaacgc gcggggagag gcggtttgcg tattgggcgc   3900
tcttccgctt cctcgctcac tgactcgctg cgctcggtcg ttcggctgcg gcgagcggta   3960
tcagctcact caaaggcggt aatacggtta tccacagaat caggggataa cgcaggaaag   4020
aacatgtgag caaaaggcca gcaaaaggcc aggaaccgta aaaaggccgc gttgctggcg   4080 ttttccata ggctccgccc ccctgacgag catcacaaaa atcgacgctc aagtcagagg    4140
tggcgaaacc cgacaggact ataaagatac caggcgtttc cccctggaag ctccctcgtg   4200
cgctctcctg ttccgaccct gccgcttacc ggatacctgt ccgcctttct cccttcggga   4260
agcgtggcgc tttctcatag ctcacgctgt aggtatctca gttcggtgta ggtcgttcgc   4320
tccaagctgg gctgtgtgca cgaaccccc gttcagcccg accgctgcgc cttatccggt     4380
aactatcgtc ttgagtccaa cccggtaaga cacgacttat cgccactggc agcagccact   4440
ggtaacagga ttagcagagc gaggtatgta ggcggtgcta cagagttctt gaagtggtgg   4500
cctaactacg gctacactag aaggacagta tttggtatct gcgctctgct gaagccagtt   4560
accttcggaa aaagagttgg tagctcttga tccggcaaac aaaccaccgc tggtagcggt   4620
ggtttttttg tttgcaagca gcagattacg cgcagaaaaa aaggatctca agaagatcct   4680
ttgatctttt ctacggggtc tgacgctcag tggaacgaaa actcacgtta agggattttg   4740
gtcatgagat tatcaaaaag gatcttcacc tagatccttt taaattaaaa atgaagtttt   4800
aaatcaatct aaagtatata tgagtaaact tggtctgaca gttaccaatg cttaatcagt   4860
gaggcaccta tctcagcgat ctgtctattt cgttcatcca tagttgcctg actccccgtc   4920
gtgtagataa ctacgatacg ggagggctta ccatctggcc ccagtgctgc aatgataccg   4980
cgagacccac gctcaccggc tccagattta tcagcaataa accagccagc cggaagggcc   5040
```

```
gagcgcagaa gtggtcctgc aactttatcc gcctccatcc agtctattaa ttgttgccgg      5100
gaagctagag taagtagttc gccagttaat agtttgcgca acgttgttgc cattgctaca      5160
ggcatcgtgg tgtcacgctc gtcgtttggt atggcttcat tcagctccgg ttcccaacga      5220
tcaaggcgag ttacatgatc ccccatgttg tgcaaaaaag cggttagctc cttcggtcct      5280
ccgatcgttg tcagaagtaa gttggccgca gtgttatcac tcatggttat ggcagcactg      5340
cataattctc ttactgtcat gccatccgta agatgctttt ctgtgactgg tgagtactca      5400
accaagtcat tctgagaata gtgtatgcgg cgaccgagtt gctcttgccc ggcgtcaata      5460
cgggataata ccgcgccaca tagcagaact ttaaaagtgc tcatcattgg aaaacgttct      5520
tcggggcgaa aactctcaag gatcttaccg ctgttgagat ccagttcgat gtaacccact      5580
cgtgcaccca actgatcttc agcatctttt actttcacca gcgtttctgg gtgagcaaaa      5640
acaggaaggc aaaatgccgc aaaaaaggga ataagggcga cacggaaatg ttgaatactc      5700
atactcttcc ttttcaata ttattgaagc atttatcagg gttattgtct catgagcgga      5760
tacatatttg aatgtattta gaaaaataaa caaataggg ttccgcgcac atttccccga      5820
aaagtgccac ctgacgtcta agaaaccatt attatcatga cattaaccta taaaaatagg      5880
cgtatcacga ggccctttcg tc                                               5902
```

<210> SEQ ID NO 4
<211> LENGTH: 319
<212> TYPE: PRT
<213> ORGANISM: Arthrospira maxima

<400> SEQUENCE: 4

```
Met Pro Phe Thr Ile Asp Ser Ala Arg Ser Ile Phe Pro Glu Thr Leu
1               5                   10                  15

Ala Ala Asp Val Val Pro Ala Thr Ile Ala Arg Phe Lys Gln Leu Ser
                20                  25                  30

Ala Glu Asp Gln Leu Ala Leu Ile Trp Phe Ala Tyr Leu Glu Met Gly
            35                  40                  45

Lys Thr Ile Thr Ile Ala Ala Pro Gly Ala Ala Asn Met Gln Phe Ala
        50                  55                  60

Glu Lys Thr Leu Glu Glu Ile Arg Gln Met Thr Pro Leu Gln Gln Thr
65                  70                  75                  80

Gln Ala Met Cys Asp Leu Ala Asn Arg Thr Asp Thr Pro Ile Cys Arg
                85                  90                  95

Thr Tyr Ala Ser Trp Ser Pro Asn Ile Lys Leu Gly Phe Trp Tyr Glu
                100                 105                 110

Leu Gly Arg Phe Met Asp Gln Gly Leu Val Ala Pro Ile Pro Glu Gly
                115                 120                 125

Tyr Lys Leu Ser Ala Asn Ala Asn Ala Ile Leu Val Thr Ile Gln Gly
            130                 135                 140

Ile Asp Pro Gly Gln Gln Ile Thr Val Leu Arg Asn Cys Val Val Asp
145                 150                 155                 160

Met Gly Phe Asp Thr Ser Lys Leu Gly Ser Tyr Gln Arg Val Ala Glu
                165                 170                 175

Pro Val Pro Pro Gln Glu Met Ser Gln Arg Thr Lys Val Gln Ile
            180                 185                 190

Glu Gly Val Thr Asn Ser Thr Val Leu Gln Tyr Met Asp Asn Leu Asn
        195                 200                 205

Ala Asn Asp Phe Asp Asn Leu Ile Ser Leu Phe Ala Glu Asp Gly Ala
    210                 215                 220
```

```
Leu Gln Pro Pro Phe Gln Lys Pro Ile Val Gly Arg Asp Asn Val Leu
225                 230                 235                 240

Arg Phe Phe Arg Glu Glu Cys Gln Asn Leu Lys Leu Ile Pro Glu Arg
                245                 250                 255

Gly Val Ser Glu Pro Thr Glu Asp Gly Tyr Thr Gln Ile Lys Val Thr
            260                 265                 270

Gly Lys Val Gln Thr Pro Trp Phe Gly Gly Asn Val Gly Met Asn Ile
        275                 280                 285

Ala Trp Arg Phe Leu Leu Asn Pro Glu Asn Lys Val Phe Phe Val Ala
    290                 295                 300

Ile Asp Leu Leu Ala Ser Pro Lys Glu Leu Leu Asn Leu Val Arg
305                 310                 315
```

<210> SEQ ID NO 5
<211> LENGTH: 320
<212> TYPE: PRT
<213> ORGANISM: Microcystis aeruginosa

<400> SEQUENCE: 5

```
Met Pro Phe Thr Ile Glu Ser Ala Arg Ser Ile Phe Pro Asn Thr Leu
1               5                   10                  15

Ser Ala Asp Val Val Pro Ala Thr Ile Ala Arg Phe Asn Gln Leu Asn
                20                  25                  30

Thr Glu Asp Gln Leu Ala Leu Ile Trp Phe Ala Tyr Leu Glu Met Gly
            35                  40                  45

Lys Thr Ile Thr Val Ala Ala Pro Gly Ala Ala Ser Met Val Phe Ala
        50                  55                  60

Glu Lys Thr Met Asn Glu Ile Arg Gln Met Ser Pro Leu Gln Gln Ser
65                  70                  75                  80

Gln Val Met Cys Asp Leu Ala Asn His Ala Asp Thr Pro Ile Cys Arg
                85                  90                  95

Thr Tyr Gly Thr Trp Ser Ala Asn Ile Lys Leu Gly Phe Trp Tyr Gln
            100                 105                 110

Leu Gly Gln Trp Met Glu Asp Gly Ser Val Ala Pro Ile Pro Lys Gly
        115                 120                 125

Tyr Gln Leu Ser Ala Asn Ala Ser Ala Val Leu Asp Gly Ile Lys Lys
    130                 135                 140

Leu Glu Ser Gly Gln Gln Ile Thr Val Leu Arg Asn Cys Val Val Asp
145                 150                 155                 160

Met Gly Tyr Asp Pro Lys Lys Leu Gly Asp Tyr Asn Arg Ile Ser Glu
                165                 170                 175

Pro Val Pro Pro Gln Asn Ile Ala Glu Arg Thr Lys Val Ser Ile
            180                 185                 190

Glu Gly Val Thr Asn Ala Thr Val Leu Asn Tyr Met Asp Asn Leu Asn
        195                 200                 205

Ala Asn Asp Phe Asp Val Leu Ile Glu Leu Phe Thr Pro Asp Gly Ala
    210                 215                 220

Leu Gln Pro Pro Phe Gln Arg Pro Ile Val Gly Lys Glu Ala Val Tyr
225                 230                 235                 240

Arg Phe Phe Arg Glu Glu Cys Gln Asn Leu Lys Leu Ile Pro Glu Cys
                245                 250                 255

Gly Val Val Glu Pro Ala Asp Asp Gly Phe Thr Gln Ile Lys Val Thr
            260                 265                 270

Gly Lys Val Gln Thr Pro Trp Phe Gly Ala Gly Val Gly Met Asn Met
```

```
                275                 280                 285
Ala Trp Arg Phe Leu Leu Thr Pro Asp Asn Lys Ile Phe Phe Val Ala
        290                 295                 300

Ile Asp Leu Leu Ala Ser Pro Lys Glu Leu Leu Asn Phe Ala Arg Gly
305                 310                 315                 320

<210> SEQ ID NO 6
<211> LENGTH: 319
<212> TYPE: PRT
<213> ORGANISM: Lyngbya PCC8106

<400> SEQUENCE: 6

Met Pro Phe Thr Ile Asp Ser Ala Arg Asn Ile Phe Pro Asn Thr Leu
1               5                   10                  15

Ala Ala Asp Thr Val Pro Ala Thr Ile Ala Arg Phe Thr Gln Leu Ser
            20                  25                  30

Ala Glu Asp Gln Leu Ala Leu Ile Trp Phe Ala Tyr Leu Glu Met Gly
        35                  40                  45

Lys Thr Ile Thr Ile Ala Ala Pro Gly Ala Ala Asn Met Gln Phe Ala
    50                  55                  60

Glu Leu Thr Leu Asn Glu Ile Arg Lys Met Gly Pro Gln Glu Gln Ser
65                  70                  75                  80

Gln Val Met Cys Asp Leu Ala Asn Arg Ser Asp Lys Pro Leu Cys Arg
                85                  90                  95

Thr Tyr Ala Thr Trp Ser Ala Asn Ile Lys Leu Gly Phe Trp Tyr Gln
            100                 105                 110

Leu Gly Gln Trp Met Asp Glu Gly Leu Val Ala Pro Ile Pro Glu Gly
        115                 120                 125

Tyr Gln Leu Ser Ala Asn Ala Ala Val Leu Gln Ala Ile Arg Gly
    130                 135                 140

Leu Glu Ser Gly Gln Gln Ile Thr Val Leu Arg Asn Ser Val Val Asp
145                 150                 155                 160

Met Gly Phe Asp Thr Ser Lys Leu Gly Ser Tyr Thr Arg Val Ala Glu
                165                 170                 175

Pro Val Thr Pro Pro Thr Asp Met Ala Lys Arg Thr Gln Val Lys Ile
            180                 185                 190

Glu Gly Val Thr Asn Ala Thr Val Leu Glu Tyr Met Asn Asn Leu Asn
        195                 200                 205

Ala Asn Asp Phe Asn Ala Leu Ile Glu Leu Phe Ala Pro Asp Gly Ala
    210                 215                 220

Leu Gln Pro Pro Phe Arg Arg Pro Ile Val Gly Lys Glu Ala Val Leu
225                 230                 235                 240

Arg Phe Phe Gln Glu Glu Cys Gln Asn Leu Lys Leu Ile Pro Glu Arg
                245                 250                 255

Gly Val Ser Glu Pro Ala Asp Glu Gly Tyr Thr Gln Ile Lys Val Thr
            260                 265                 270

Gly Lys Val Gln Thr Pro Trp Phe Gly Ala Gly Val Gly Met Asn Ile
        275                 280                 285

Ala Trp Arg Phe Leu Leu Asn Ala Glu Asn Lys Ile Phe Phe Val Ala
    290                 295                 300

Ile Asp Leu Leu Ala Ser Pro Lys Glu Leu Leu Asn Phe Ala Arg
305                 310                 315

<210> SEQ ID NO 7
<211> LENGTH: 319
```

<212> TYPE: PRT
<213> ORGANISM: Cyanothece PCC7424

<400> SEQUENCE: 7

Met Pro Phe Thr Ile Asp Ser Ala Arg Asn Ile Phe Pro Gly Thr Leu
1               5                   10                  15

Ala Ala Asp Ala Val Pro Ala Thr Ile Ala Arg Phe Asn Gln Leu Ser
            20                  25                  30

Ala Glu Asp Gln Leu Ala Leu Ile Trp Phe Ala Tyr Leu Glu Met Gly
        35                  40                  45

Lys Thr Ile Thr Ile Ala Ala Pro Gly Ala Ala Ser Met Val Phe Ala
    50                  55                  60

Glu Asn Thr Leu Lys Glu Ile Gln Gln Met Thr Pro Leu Gln Gln Thr
65                  70                  75                  80

Gln Val Met Cys Asp Leu Thr Asn Arg Ala Asp Thr Pro Ile Cys Arg
                85                  90                  95

Thr Tyr Ala Thr Trp Ser Pro Asn Ile Lys Leu Gly Phe Trp Tyr Arg
            100                 105                 110

Leu Gly Glu Leu Met Glu Gln Gly Leu Val Ala Pro Ile Pro Lys Gly
        115                 120                 125

Tyr Gln Leu Ser Ala Asn Ala Asn Ala Val Leu Glu Ala Ile Lys Ser
    130                 135                 140

Leu Glu Ser Gly Gln Gln Ile Thr Val Leu Arg Asn Cys Val Val Asp
145                 150                 155                 160

Met Gly Phe Glu Pro Ser Lys Leu Gly Asn Tyr Thr Arg Val Ala Glu
                165                 170                 175

Pro Val Glu Pro Pro Lys Glu Met Ser Gln Arg Thr Gln Val Tyr Ile
            180                 185                 190

Asp Gly Val Ser Asn Pro Thr Val Leu Asp Tyr Met Asn Asn Leu Asn
        195                 200                 205

Ala Asn Asp Phe Glu Ala Leu Ile Glu Leu Phe Thr Pro Asp Gly Gly
    210                 215                 220

Leu Gln Pro Pro Phe Gln Arg Pro Ile Val Gly Lys Glu Ala Ile Leu
225                 230                 235                 240

Arg Phe Phe Lys Glu Glu Cys Gln Asn Leu Lys Leu Ile Pro Glu Lys
                245                 250                 255

Gly Val Ser Glu Pro Thr Asp Asp Gly Tyr Thr Gln Ile Lys Val Thr
            260                 265                 270

Gly Lys Val Gln Thr Pro Trp Phe Gly Ala Asn Val Gly Met Asn Ile
        275                 280                 285

Ala Trp Arg Phe Leu Leu Asn Pro Asp Asn Lys Ile Phe Phe Val Ala
    290                 295                 300

Ile Asp Leu Leu Ala Ser Pro Lys Glu Leu Leu Asn Phe Ala Arg
305                 310                 315

<210> SEQ ID NO 8
<211> LENGTH: 319
<212> TYPE: PRT
<213> ORGANISM: Cyanothece CCY0110

<400> SEQUENCE: 8

Met Pro Phe Ser Ile Asp Ser Ala Arg Asn Ile Phe Pro Asn Thr Leu
1               5                   10                  15

Ala Ala Asp Ala Val Pro Ala Thr Ile Ala Arg Phe Glu Gln Leu Ser
            20                  25                  30

```
Ala Glu Asp Gln Leu Ala Leu Ile Trp Phe Ala Tyr Leu Glu Met Gly
            35                  40                  45

Lys Asn Ile Thr Val Ala Ala Pro Gly Ala Ala Asn Met Gln Phe Ala
        50                  55                  60

Glu Gly Thr Ile Lys Glu Ile Ile Asn Met Thr Pro Leu Glu Gln Ser
65                  70                  75                  80

Gln Ala Met Cys Asp Leu Ala Asn Arg Ala Asp Thr Pro Ile Ser Arg
                85                  90                  95

Thr Tyr Ala Thr Trp Ser Pro Asn Ile Lys Leu Gly Phe Trp Tyr Glu
            100                 105                 110

Leu Gly Lys Leu Met Glu Glu Gly Lys Val Ala Pro Ile Pro Lys Gly
        115                 120                 125

Tyr Lys Leu Ser Ala Asn Ala Asn Ser Val Leu Val Thr Ile Thr Gly
130                 135                 140

Leu Glu Pro Gly Gln Gln Ile Thr Val Leu Arg Asn Cys Val Val Asp
145                 150                 155                 160

Met Gly Tyr Asp Pro Ser Lys Met Ser Asn Phe Gln Lys Val Thr Glu
                165                 170                 175

Pro Val Ala Pro Pro Lys Glu Met Ser Gln Arg Thr Gln Val Lys Ile
            180                 185                 190

Glu Gly Ile Asp Asn Ser Thr Ile Leu Asn Tyr Met Asn Asn Leu Asn
        195                 200                 205

Ala Asn Asp Phe Asp Ala Leu Ile Ala Leu Phe Thr Glu Asp Gly Ala
210                 215                 220

Leu Gln Pro Pro Phe Arg Arg Pro Ile Ile Gly Lys Glu Asn Val Leu
225                 230                 235                 240

Arg Phe Phe Arg Glu Glu Cys Gln Asn Leu Gln Leu Ile Pro Lys Gln
                245                 250                 255

Gly Val Ser Glu Pro Ala Glu Asp Gly Phe Thr Gln Ile Lys Val Thr
            260                 265                 270

Gly Thr Cys Gln Thr Pro Trp Phe Gly Gly Val Gly Met Asn Ile
        275                 280                 285

Ala Trp Arg Phe Leu Leu Asn Pro Glu Gly Lys Ile Phe Phe Val Ala
290                 295                 300

Ile Asp Leu Leu Ala Ser Pro Lys Glu Leu Leu Asn Leu Ala Arg
305                 310                 315

<210> SEQ ID NO 9
<211> LENGTH: 319
<212> TYPE: PRT
<213> ORGANISM: Cyanothece ATCC51142

<400> SEQUENCE: 9

Met Pro Phe Thr Leu Asp Ser Ala Arg Asn Ile Phe Pro Asn Thr Leu
1               5                   10                  15

Ala Ala Asp Ala Val Pro Ala Thr Ile Ala Arg Phe Glu Gln Leu Ser
            20                  25                  30

Ala Glu Asp Gln Leu Ala Leu Ile Trp Phe Ala Tyr Leu Glu Met Gly
        35                  40                  45

Lys Asn Ile Thr Val Ala Ala Pro Gly Ala Ala Asn Met Gln Phe Ala
    50                  55                  60

Glu Gly Thr Ile Lys Glu Ile Ile Asn Met Thr Pro Leu Glu Gln Ser
65                  70                  75                  80

Gln Ala Met Cys Asp Leu Ala Asn Arg Ala Asp Thr Ala Ile Ser Arg
                85                  90                  95
```

```
Thr Tyr Ala Thr Trp Ser Pro Asn Ile Lys Leu Gly Phe Trp Tyr Glu
            100                 105                 110

Leu Gly Lys Leu Met Glu Gln Gly Lys Val Ala Pro Ile Pro Glu Gly
            115                 120                 125

Tyr Lys Leu Ser Ala Asn Ala Asn Ala Val Leu Leu Thr Ile Thr Gly
130                 135                 140

Leu Glu Pro Gly Gln Gln Ile Thr Val Leu Arg Asn Cys Val Asp
145                 150                 155                 160

Met Gly Tyr Asp Pro Ser Lys Met Gly Asn Phe Gln Lys Ile Thr Glu
                165                 170                 175

Pro Val Ala Pro Pro Lys Glu Met Ala Gln Arg Thr Gln Val Lys Ile
                180                 185                 190

Glu Gly Val Asp Asn Ser Thr Ile Leu Ser Tyr Met Asn Asn Leu Asn
                195                 200                 205

Ala Asn Asp Phe Asp Ala Leu Ile Lys Leu Phe Ala Glu Asp Gly Ala
            210                 215                 220

Leu Gln Pro Pro Phe Arg Arg Pro Ile Ile Gly Lys Glu Asn Val Leu
225                 230                 235                 240

Arg Phe Phe Arg Glu Glu Cys Gln Asn Leu Gln Leu Ile Pro Lys Gln
                245                 250                 255

Gly Val Ser Glu Pro Ala Glu Asp Gly Phe Thr Gln Ile Lys Val Thr
                260                 265                 270

Gly Thr Cys Gln Thr Pro Trp Phe Gly Gly Val Gly Met Asn Ile
                275                 280                 285

Ala Trp Arg Phe Leu Leu Asn Pro Glu Gly Lys Ile Phe Phe Val Ala
            290                 295                 300

Ile Asp Leu Leu Ala Ser Pro Lys Glu Leu Leu Asn Leu Ala Arg
305                 310                 315

<210> SEQ ID NO 10
<211> LENGTH: 320
<212> TYPE: PRT
<213> ORGANISM: Nostoc punctiforme PCC73102

<400> SEQUENCE: 10

Met Ser Phe Thr Ile Lys Ser Ala Gln Ser Ile Phe Pro Gly Thr Leu
1               5                   10                  15

Val Ala Asp Val Val Pro Thr Val Val Glu Ser Phe Ser Gln Leu Asn
                20                  25                  30

Ala Glu Asp Gln Leu Ala Leu Leu Trp Phe Ala Tyr Thr Glu Met Gly
            35                  40                  45

Arg Ser Ile Thr Val Ala Ala Pro Gly Ala Ala Asn Met Val Leu Ala
50                  55                  60

Gln Gly Leu Leu Glu Gln Ile Lys Gln Met Pro Phe Glu Ala Gln Thr
65                  70                  75                  80

Arg Val Met Tyr Asp Leu Ala Asn Arg Ala Asp Thr Pro Leu Cys Arg
                85                  90                  95

Ser Tyr Ala Ser Phe Thr Val Asn Ile Lys Leu Gly Phe Trp Tyr Gln
            100                 105                 110

Leu Gly Glu Trp Met Ala Gln Gly Ile Val Ala Pro Ile Pro Glu Gly
            115                 120                 125

Tyr Lys Leu Ser Pro Lys Ala Ala Asp Val Leu Glu Ala Ile Arg Asn
130                 135                 140

Ala Asp Ser Gly Gln Gln Ile Thr Ile Leu Arg Asn Thr Val Val Ser
```

```
                145                 150                 155                 160
        Met Gly Phe Asp Pro Asn Ala Pro Gly Ser Tyr Lys Lys Val Ser Glu
                        165                 170                 175

Pro Val Ala Pro Thr Ala Pro Ala Phe Arg Thr Lys Val Ser Ile
                    180                 185                 190

Glu Gly Ile Asn Asn Pro Thr Val Leu Gly Tyr Ile Asn Asn Met Asn
                        195                 200                 205

Ala Asn Asp Phe Asp Ala Ala Val Ala Leu Phe Thr Ser Glu Gly Gly
                    210                 215                 220

Leu Gln Pro Pro Phe Glu Arg Pro Ile Ile Gly Gln Asp Ala Ile Arg
        225                 230                 235                 240

Ala Tyr Met Arg Glu Glu Cys Gln Gly Leu Lys Met Ile Pro Glu Arg
                        245                 250                 255

Gly Ile Ser Glu Pro Val Glu Asp Gly Tyr Thr Gln Val Lys Val Thr
                        260                 265                 270

Gly Lys Val Gln Thr Pro Trp Phe Gly Ala Ser Val Gly Met Asn Ile
                    275                 280                 285

Ala Trp Arg Phe Leu Leu Asp Pro Gln Gly Lys Ile Phe Val Ala
                    290                 295                 300

Ile Asp Leu Leu Ala Ser Pro Lys Glu Leu Leu Asn Leu Val Arg Lys
        305                 310                 315                 320

<210> SEQ ID NO 11
<211> LENGTH: 319
<212> TYPE: PRT
<213> ORGANISM: Nostoc PCC7120

<400> SEQUENCE: 11

Met Ala Ile Thr Ile Asp Ser Ala Arg Arg Ile Phe Pro Asn Thr Leu
        1               5                   10                  15

Gln Ala Asp Ala Val Pro Ala Leu Thr Ala Arg Phe Asn Gln Leu Ser
                        20                  25                  30

Ala Glu Asp Gln Leu Ala Trp Thr Trp Phe Ala Phe Leu Glu Met Gly
                    35                  40                  45

Lys Thr Ile Thr Val Ala Ala Pro Gly Ala Ala Ser Met Gln Phe Ala
                50                  55                  60

Glu Gly Ile Leu Lys Gln Ile Lys Glu Met Thr Phe Glu Glu Gln Thr
        65                  70                  75                  80

Gln Val Met Cys Asp Leu Ala Asn His Thr Asp Thr Pro Ile Cys Arg
                        85                  90                  95

Thr Tyr Ala Thr Trp Ser Pro Asn Ile Lys Leu Gly Phe Trp Asn Gln
                    100                 105                 110

Leu Gly Glu Trp Met Glu Gln Gly Ala Val Ala Pro Ile Pro Ala Gly
                    115                 120                 125

Tyr Gln Leu Ser Ala Asn Ala Asn Ala Val Leu Glu Thr Leu Lys Ser
                130                 135                 140

Leu Asp Gln Gly Gln Gln Ile Thr Val Leu Arg Ser Ser Val Val Asp
        145                 150                 155                 160

Met Gly Phe Asp Ala Ala Lys Leu Asp Gly Tyr Thr Arg Val Ala Glu
                        165                 170                 175

Pro Leu Val Ala Pro Lys Asp Ile Ser Gln Arg Val Gln Val Thr Ile
                    180                 185                 190

Glu Gly Ile Asn Asn Ser Thr Val Leu Asn Tyr Met Asn Asn Leu Asn
                        195                 200                 205
```

Ala Asn Asp Phe Asp Glu Leu Ile Lys Leu Phe Val Glu Asp Gly Ala
210                 215                 220

Leu Gln Pro Pro Phe Gln Arg Pro Ile Val Gly Lys Asp Ala Ile Leu
225                 230                 235                 240

Arg Phe Phe Arg Glu Glu Cys Gln Asn Leu Asn Leu Leu Pro Glu Arg
                245                 250                 255

Gly Val Ala Glu Pro Ala Asp Asp Gly Tyr Thr Gln Val Lys Val Thr
            260                 265                 270

Gly Lys Val Gln Thr Pro Trp Phe Gly Ala Ala Val Gly Met Asn Met
                275                 280                 285

Ala Trp Arg Phe Leu Leu Asn Pro Gln Gly Lys Ile Phe Phe Val Ala
290                 295                 300

Ile Asp Leu Leu Ala Ser Pro Lys Glu Leu Leu Asn Leu Val Arg
305                 310                 315

<210> SEQ ID NO 12
<211> LENGTH: 319
<212> TYPE: PRT
<213> ORGANISM: Anabaena variabilis ATCC29413

<400> SEQUENCE: 12

Met Ala Ile Thr Ile Asp Ser Ala Arg Arg Ile Phe Pro Asn Thr Leu
1               5                   10                  15

Gln Ala Asp Ala Val Pro Ala Leu Thr Ala Arg Phe Asn Gln Leu Ser
                20                  25                  30

Ala Glu Asp Gln Leu Ala Trp Thr Trp Phe Ala Phe Leu Glu Met Gly
            35                  40                  45

Lys Thr Ile Thr Val Ala Ala Pro Gly Ala Ala Ser Met Gln Phe Ala
50                  55                  60

Glu Gly Ile Leu Lys Gln Ile Lys Glu Met Thr Phe Glu Glu Gln Thr
65                  70                  75                  80

Gln Val Met Cys Asp Leu Ala Asn His Thr Asp Thr Pro Ile Cys Arg
                85                  90                  95

Thr Tyr Ala Thr Trp Ser Pro Asn Ile Lys Leu Gly Phe Trp Asn Gln
            100                 105                 110

Leu Gly Glu Trp Met Glu Gln Gly Val Val Ala Pro Ile Pro Ala Gly
        115                 120                 125

Tyr Gln Leu Ser Ala Asn Ala Asn Ala Val Leu Glu Thr Leu Lys Ser
    130                 135                 140

Leu Asp Gln Gly Gln Gln Ile Thr Val Leu Arg Ser Ser Val Val Asp
145                 150                 155                 160

Met Gly Phe Asp Ala Ala Lys Leu Gly Gly Tyr Thr Arg Val Ser Glu
                165                 170                 175

Pro Val Val Ala Pro Lys Asp Ile Ser Gln Arg Val Gln Val Ser Ile
            180                 185                 190

Glu Gly Ile Asn Asn Pro Thr Val Leu Asn Tyr Met Asn Asn Leu Asn
        195                 200                 205

Ala Asn Asp Phe Asp Glu Leu Ile Lys Leu Phe Val Glu Asp Gly Ala
210                 215                 220

Leu Gln Pro Pro Phe Gln Arg Pro Ile Val Gly Lys Asp Ala Ile Leu
225                 230                 235                 240

Arg Phe Phe Arg Glu Glu Cys Gln Asn Leu Asn Leu Leu Pro Glu Arg
                245                 250                 255

Gly Val Ala Glu Pro Ala Glu Asp Gly Tyr Thr Gln Val Lys Val Thr
            260                 265                 270

```
Gly Lys Val Gln Thr Pro Trp Phe Gly Ala Ala Val Gly Met Asn Met
            275                 280                 285

Ala Trp Arg Phe Leu Leu Asn Pro Gln Gly Lys Ile Phe Phe Val Ala
290                 295                 300

Ile Asp Leu Leu Ala Ser Pro Lys Glu Leu Leu Asn Leu Val Arg
305                 310                 315

<210> SEQ ID NO 13
<211> LENGTH: 319
<212> TYPE: PRT
<213> ORGANISM: Oscillatoria PCC6506

<400> SEQUENCE: 13

Met Pro Phe Thr Ile Glu Thr Ala Gln Gly Ile Phe Ser Asn Thr Gln
1               5                   10                  15

Val Ala Ser Ala Val Pro Asp Thr Ile Ala Lys Phe Ala Gln Leu Ser
            20                  25                  30

Ala Glu Asp Gln Leu Ala Leu Leu Trp Phe Ala Tyr Thr Glu Met Gly
        35                  40                  45

Ile Thr Ile Thr Pro Ala Ala Pro Gly Ala Ala Ser Met Val Ile Ala
50                  55                  60

Asp Gly Leu Leu Ala Gln Ile Lys Gln Met Pro Pro Leu Ala Gln Thr
65                  70                  75                  80

Gln Val Met Cys Asp Leu Ala Asn Arg Val Asp Thr Pro Leu Asn Arg
                85                  90                  95

Ser Tyr Ala Ser Phe Ser Met Asn Ile Lys Leu Gly Phe Trp Tyr Gln
            100                 105                 110

Leu Gly Glu Trp Met Ala Gln Gly Leu Val Ala Pro Ile Pro Pro Gly
        115                 120                 125

Tyr Lys Leu Ser Ser Asn Ala Ser Ala Val Leu Gln Thr Ile Arg Gln
130                 135                 140

Leu Asp Gly Gly Gln Gln Ile Thr Val Leu Arg Asn Ala Val Val Asn
145                 150                 155                 160

Met Gly Phe Asp Pro Asn Ala Pro Gly Ser Tyr Ala Lys Val Ala Asp
                165                 170                 175

Pro Val Pro Pro Thr Glu Ile Ala Gln Arg Thr Gln Val Thr Ile
            180                 185                 190

Glu Gly Val Thr Asn Pro Thr Val Leu Gly Tyr Ile Asn Asn Met Asn
        195                 200                 205

Ala Phe Asp Phe Glu Ala Ala Val Gly Leu Phe Ala Pro Lys Gly Ala
210                 215                 220

Leu Gln Pro Pro Phe Gln Lys Pro Ile Val Gly Gln Glu Ala Ile Leu
225                 230                 235                 240

Ala Tyr Met Arg Glu Glu Cys Val Gly Leu Lys Met Met Pro Glu Arg
                245                 250                 255

Gly Val Ser Glu Val Val Asp Gly Tyr Thr Gln Ile Lys Val Thr Gly
            260                 265                 270

Lys Val Gln Thr Pro Trp Phe Gly Ala Ser Val Gly Met Asn Ile Ala
        275                 280                 285

Trp Arg Phe Leu Ile Asp Pro Gln Gly Lys Ile Phe Phe Val Ala Ile
290                 295                 300

Asp Leu Leu Ala Ser Pro Gln Glu Leu Leu Asn Leu Met Ala Lys
305                 310                 315
```

-continued

```
<210> SEQ ID NO 14
<211> LENGTH: 281
<212> TYPE: PRT
<213> ORGANISM: Microcoleus chthonoplastes PCC7420

<400> SEQUENCE: 14
```

Ala Leu Ile Trp Phe Ala Tyr Leu Glu Met Gly Lys Thr Ile Thr Ile
1               5                   10                  15

Ala Ala Pro Gly Ala Ala Ser Met Val Leu Ala Glu Pro Thr Leu Asn
            20                  25                  30

Gln Ile Lys Gln Met Ser Phe Gln Glu Gln Thr Gln Val Met Cys Asp
        35                  40                  45

Leu Ala Asn Arg Ala Asp Ala Pro Ile Ser Arg Thr Tyr Ala Ser Trp
    50                  55                  60

Ser Ala Asn Ile Lys Leu Gly Phe Trp Tyr Gln Leu Gly Gln Trp Met
65                  70                  75                  80

Glu Gln Gly Thr Val Ala Pro Ile Pro Glu Gly Tyr Arg Leu Ser Ala
                85                  90                  95

Asn Ala Ser Ala Val Leu Gln Ala Ile Arg Asn Leu Asp Pro Gly Gln
            100                 105                 110

Gln Ile Thr Val Leu Arg Asn Ala Val Val Asp Met Gly Phe Asp Pro
        115                 120                 125

Ser Lys Leu Gly Ser Tyr Lys Lys Val Thr Glu Pro Ile Val Pro Pro
    130                 135                 140

Lys Asp Met Ser Gln Arg Thr Ser Val Ala Ile Gln Gly Val Asp Asn
145                 150                 155                 160

Pro Thr Val Leu Ser Tyr Met Asn Tyr Met Asn Ala Asn Asp Phe Asp
                165                 170                 175

Ala Leu Ile Gln Met Phe Thr Asp Asp Gly Ala Leu Gln Pro Pro Phe
            180                 185                 190

Gln Arg Pro Ile Ile Gly Lys Asp Ala Val Tyr Arg Phe Phe Arg Glu
        195                 200                 205

Glu Cys Gln Asn Leu Lys Leu Leu Pro Glu His Gly Val Ser Glu Pro
    210                 215                 220

Thr Glu Glu Gly Tyr Thr Gln Ile Lys Val Thr Gly Lys Val Gln Thr
225                 230                 235                 240

Pro Trp Phe Gly Ala Gly Val Gly Met Asn Met Ala Trp Arg Phe Leu
                245                 250                 255

Leu Asn Pro Glu Asn Lys Ile Tyr Phe Val Ala Ile Asp Leu Leu Ala
            260                 265                 270

Ser Pro Lys Glu Leu Leu Asn Ala Arg
        275                 280

```
<210> SEQ ID NO 15
<211> LENGTH: 274
<212> TYPE: PRT
<213> ORGANISM: Gloeobacter violaceus PCC7421

<400> SEQUENCE: 15
```

Met Thr Pro Ala Ala Leu Ser Ala Ser Ser Met Phe Leu Ile Glu Asp
1               5                   10                  15

Leu Leu Asp Arg Ile Gln Arg Met Ser Gly Pro Glu Gln Thr Gln Val
            20                  25                  30

Met Phe Asp Leu Val Arg Arg Ala Asp Ser Pro Ile Ser Arg Ser Tyr
        35                  40                  45

Ser Ser Tyr Ser Ala Asn Thr Lys Leu Gly Phe Trp Tyr Gln Leu Ala

```
                50                  55                  60
Arg Trp Met Ala Asp Gly Leu Val Ala Pro Ile Gln Tyr Gly Tyr Glu
 65                  70                  75                  80

Leu Ser Ser Gln Gly Gln Glu Leu Phe Glu Thr Leu Lys Gln Leu Asp
                 85                  90                  95

Gly Gly Gln Gln Ile Gln Ile Leu Arg Asp Ile Val Val Asn Met Gly
            100                 105                 110

Tyr Asp Pro Ser Ile Ala Lys Val Ala Ala Glu Pro Val Glu Phe Asp
            115                 120                 125

Phe Ile Arg Thr Glu Pro Val Ala Ala Lys Pro His Ile Glu Gly
        130                 135                 140

Ile Lys Glu Pro Val Val Leu Ala Tyr Phe Glu Ala Met Asn Thr Asp
145                 150                 155                 160

Asn Phe Asp Ala Ala Val Ala Leu Phe Ala Pro Asp Gly Ala Leu Gln
                165                 170                 175

Pro Pro Phe Arg Glu Pro Ile Val Gly His Gln Ala Ile Ala Ala Tyr
            180                 185                 190

Met Arg Glu Glu Ala Lys Gly Leu Thr Leu Met Pro Gln Gln Gly Ile
        195                 200                 205

Ser Gln Val Leu Gly Asp Gly Ser Lys Gln Leu Lys Ile Thr Gly Lys
210                 215                 220

Val Gln Thr Pro Trp Phe Gly Val Asn Val Ala Met Asn Ile Ala Trp
225                 230                 235                 240

Arg Phe Ala Leu Asn Pro Glu Gly Lys Ile Phe Tyr Val Gly Ile Asp
                245                 250                 255

Leu Leu Ala Ser Pro Gln Glu Leu Leu Asn Leu Arg Pro Asp Lys Leu
            260                 265                 270

Ala Arg

<210> SEQ ID NO 16
<211> LENGTH: 322
<212> TYPE: PRT
<213> ORGANISM: Nodularia spumigena CCY9414

<400> SEQUENCE: 16

Met Ala Leu Thr Ile Gln Ser Ala Gln Asn Ile Phe Ser Asn Thr Gln
 1               5                  10                  15

Val Pro Ser Pro Ile Pro Ala Thr Ile Ala Leu Phe Asp Gln Leu Gly
                 20                  25                  30

Val Asp Asp Gln Leu Ala Tyr Leu Trp Tyr Ala Tyr Thr Glu Met Gly
            35                  40                  45

Lys Thr Ile Thr Pro Ala Ala Pro Gly Ala Ala Arg Leu Gln Leu Ala
         50                  55                  60

Glu Ser Leu Leu Asn Gln Ile Lys Lys Met Ser Pro Glu Glu Gln Thr
 65                  70                  75                  80

Gln Val Met Arg Asp Leu Ala Asn Arg Ala Asp Ala Pro Ile Ser Arg
                 85                  90                  95

Ser Tyr Gly Phe Phe Ser Val Asn Thr Lys Leu Ala Phe Trp Tyr Glu
            100                 105                 110

Leu Gly Glu Leu Met Lys Gln Gly Val Val Ala Pro Ile Pro Ser Gly
        115                 120                 125

Tyr Gln Met Thr Pro Gly Val Gln Val Val Leu Asp Ala Thr Lys Lys
        130                 135                 140

Leu Asp Pro Gly Gln Gln Ile Thr Val Leu Arg Asn Thr Val Val Asn
```

```
                145                 150                 155                 160
Met Gly Phe Asp Thr Ser Asp Leu Gly Pro Ser Ser Tyr Pro Lys Ala
                    165                 170                 175

Val Glu Glu Pro Ala Phe Ala Arg Thr Ala Pro Ser Ile Ser Ser Val
                    180                 185                 190

Lys Ile Asp Gly Val Thr Glu Pro Ala Val Leu Ser Tyr Ile Glu Ala
                    195                 200                 205

Met Asn Ala Asp Asn Phe Asp Lys Ala Ile Ser Leu Phe Thr Pro Glu
                    210                 215                 220

Gly Ala Leu Gln Pro Pro Phe Gln Lys Pro Ile Val Gly His Glu Ala
225                 230                 235                 240

Ile Ala Lys Tyr Met Arg Glu Glu Ala Gln Gly Leu Asn Met Met Pro
                    245                 250                 255

Lys Gln Gly Ile Cys Glu Asp Gln Pro Asp Gly Ser Lys Gln Leu Lys
                    260                 265                 270

Ile Thr Gly Val Val Gln Thr Pro Trp Phe Gly Val Thr Val Gly Met
                    275                 280                 285

Asn Ile Ala Trp Arg Phe Leu Ile Asn Pro Glu Gly Lys Ile Phe Phe
                    290                 295                 300

Val Ala Ile Asp Met Leu Ala Ser Pro Glu Glu Leu Leu Asn Leu Arg
305                 310                 315                 320

Arg Val

<210> SEQ ID NO 17
<211> LENGTH: 319
<212> TYPE: PRT
<213> ORGANISM: Cylindrospermopsis raciborskii CS-505

<400> SEQUENCE: 17

Met Ala Ile Thr

```
            195                 200                 205
Ala Asn Asp Phe Gly Ala Leu Ile Asp Leu Phe Ala Pro Asp Gly Ala
        210                 215                 220

Leu Gln Pro Pro Phe Gln Lys Pro Ile Val Gly Arg Asp Ala Ile Leu
225                 230                 235                 240

Arg Phe Phe Asn Glu Glu Cys Gln Asn Leu Thr Leu Val Pro Glu Arg
                245                 250                 255

Gly Val Ser Glu Pro Val Glu Asp Gly Tyr Thr Gln Ile Lys Val Thr
            260                 265                 270

Gly Lys Val Gln Thr Pro Trp Phe Gly Ser Ser Val Gly Met Asn Ile
        275                 280                 285

Ala Trp Arg Phe Leu Leu Asn Pro Gln Gly Lys Ile Phe Phe Val Ala
        290                 295                 300

Ile Asp Leu Leu Ala Ser Pro Lys Glu Leu Leu Asn Leu Met Arg
305                 310                 315

<210> SEQ ID NO 18
<211> LENGTH: 323
<212> TYPE: PRT
<213> ORGANISM: Synechococcus RS9917

<400> SEQUENCE: 18

Met Phe Thr Ile Glu Lys Ala Arg Gln Ile Phe Pro Glu Thr Arg Thr
1               5                   10                  15

Ala Asp Ala Val Pro Ala Ile Thr Ala Arg Tyr Lys Leu Leu Ser Ala
            20                  25                  30

Glu Asp Gln Leu Ala Leu Ile Trp Phe Ala Tyr Leu Glu Met Gly Arg
        35                  40                  45

Thr Ile Thr Val Ala Ala Pro Gly Ala Ala Arg Met Ala Leu Ala Lys
    50                  55                  60

Pro Thr Leu Asp Glu Ile Glu Ala Met Thr Phe Asp Glu Gln Thr Lys
65                  70                  75                  80

Val Met Cys Asp Leu Ala Ser Lys Ile Asn Ser Pro Ile Ser Lys Arg
                85                  90                  95

Tyr Ala Tyr Trp Ser Val Asn Val Lys Leu Gly Phe Trp Tyr Glu Leu
            100                 105                 110

Gly Glu Leu Met Arg Gln Gly Lys Val Ala Pro Ile Pro Gln Gly Tyr
        115                 120                 125

Lys Leu Ser Ala Asn Ala Ser Ser Val Leu Glu Ala Val Lys Lys Val
    130                 135                 140

Glu Gln Gly Gln Gln Ile Thr Leu Leu Arg Asn Phe Val Val Asp Met
145                 150                 155                 160

Gly Phe Asp Pro Asn Ile Asp Asp Lys Ile Val Ala Glu Pro Ile
                165                 170                 175

Val Ile Pro Thr Pro Ala Glu Glu Arg Glu Thr Ile Thr Ile Pro Gly
            180                 185                 190

Val Leu Asn Gln Thr Val Leu Ser Tyr Met Gln Leu Leu Asn Ala Asn
        195                 200                 205

Asp Phe Asp Gln Leu Ile Glu Leu Phe Leu Glu Asp Gly Ala Leu Gln
    210                 215                 220

Pro Pro Phe Gln Arg Pro Ile Val Gly Arg Asp Ala Ile Leu Lys Phe
225                 230                 235                 240

Phe Arg Arg Asp Cys Gln Asn Leu Lys Leu Ile Pro Arg Gly Gly Phe
                245                 250                 255
```

Gly Glu Pro Ala Glu Gly Gly Phe Asn Gln Ile Lys Val Thr Gly Lys
             260                 265                 270

Val Glu Thr Pro Trp Phe Gly Arg Glu Val Gly Met Asn Val Ala Trp
         275                 280                 285

Arg Phe Leu Leu Asp Glu Asn Asn Lys Ile Tyr Phe Val Ala Ile Asp
     290                 295                 300

Leu Leu Ala Ser Pro Asp Glu Leu Leu Lys Leu Gly Ala Asp Lys Leu
305                 310                 315                 320

Ser Gly Lys

<210> SEQ ID NO 19
<211> LENGTH: 320
<212> TYPE: PRT
<213> ORGANISM: Synechococcus PCC7002

<400> SEQUENCE: 19

Met Pro Tyr Thr Leu Asp Ala Ala Arg Asn Ile Phe Pro Ser Thr Leu
1               5                   10                  15

Thr Ala Asp Val Val Pro Ala Thr Ser Ala Arg Phe Ser Gln Leu Ser
             20                  25                  30

Ala Glu Asp Gln Leu Ala Leu Ile Trp Phe Ala Tyr Leu Glu Met Gly
         35                  40                  45

Lys Ser Ile Thr Ile Ala Ala Pro Gly Ala Ala Asn Met Gln Phe Ala
     50                  55                  60

Glu Ser Thr Leu Leu Gln Ile Lys Gln Leu Ser Phe Lys Asp Gln Ala
65                  70                  75                  80

Gln Val Met Cys Asp Leu Ala Asn Arg Ile Asp Thr Pro Ile Asn Arg
                 85                  90                  95

Thr Tyr Ala Thr Trp Ser Val Asn Ile Lys Leu Gly Phe Trp Tyr Arg
            100                 105                 110

Leu Gly Glu Trp Met Glu Gly Ser Val Ala Pro Ile Pro Ala Gly
        115                 120                 125

Tyr Lys Leu Ser Ala Asn Ala Ser Ala Val Leu Asp Thr Ile Arg Ser
    130                 135                 140

Leu Glu Pro Gly Gln Gln Ile Thr Val Leu Arg Asn Ala Val Val Asp
145                 150                 155                 160

Met Gly Phe Asp Pro Ala Lys Met Glu Gly Tyr Gln Arg Val Ser Glu
                165                 170                 175

Pro Val Val Pro Thr Glu Ile Ala Gln Arg Glu Lys Ile Glu Ile
            180                 185                 190

Glu Gly Val Asp Asn Pro Thr Ile Asn Gln Tyr Met Thr Asn Leu Asn
    195                 200                 205

Ala Asn Asp Phe Pro Ala Leu Ile Ser Leu Phe Ala Glu Asp Gly Ala
    210                 215                 220

Leu Gln Pro Pro Phe Gln Arg Pro Ile Val Gly Lys Asp Ala Val Leu
225                 230                 235                 240

Arg Phe Phe Gln Glu Glu Cys Gln Asn Leu Lys Leu Asn Pro Lys Lys
                245                 250                 255

Gly Val Val Glu Pro Thr Asp Asp Gly Tyr Thr Gln Ile Lys Val Thr
            260                 265                 270

Gly Thr Cys Glu Thr Pro Trp Phe Gly Ala Ala Val Gly Met Asn Val
        275                 280                 285

Ala Trp Arg Phe Leu Leu Asn Pro Glu Gly Lys Ile Phe Phe Val Ala
    290                 295                 300

```
Val Asp Leu Leu Ala Ser Ala Lys Glu Leu Leu Asn Leu Val Arg Lys
305                 310                 315                 320

<210> SEQ ID NO 20
<211> LENGTH: 319
<212> TYPE: PRT
<213> ORGANISM: Raphidiopsis brookii D9

<400> SEQUENCE: 20

Met Ala Ile Thr Ile Asp Ser Ala Arg Gly Ile Phe Pro Gln Thr Leu
1               5                   10                  15

Ser Ala Asp Ala Val Pro Ala Thr Ile Ala Arg Phe Lys Gln Leu Ser
                20                  25                  30

Ala Glu Asp Gln Leu Ala Trp Ile Trp Phe Ala Tyr Leu Glu Met Gly
            35                  40                  45

Lys Thr Val Thr Ile Ala Ala Pro Gly Ala Ala Ser Met Gln Phe Ala
50                  55                  60

Glu Thr Thr Leu Asn Gln Ile Arg Gln Met Ser Phe Pro Glu Gln Thr
65                  70                  75                  80

Gln Ala Met Cys Asp Leu Ala Asn Ser Ala Asp Thr Pro Ile Cys Arg
                85                  90                  95

Thr Tyr Ala Ala Trp Ser Pro Asn Ile Lys Leu Gly Phe Trp Asn Gln
            100                 105                 110

Leu Gly Glu Trp Met Glu Gln Gly Ile Val Ala Pro Ile Pro Ala Gly
        115                 120                 125

Tyr Gln Leu Ser Pro Asn Ala Ala Val Leu Gln Ala Leu Arg Glu
        130                 135                 140

Met Asp Gln Gly Gln Gln Ile Thr Thr Leu Arg Ser Thr Val Val Asp
145                 150                 155                 160

Met Gly Phe Asp Pro Asn Lys Leu Gly Asp Tyr Thr Arg Ile Ser Glu
                165                 170                 175

Pro Val Val Val Pro Thr Glu Met Ser Lys Arg Thr Gln Val Thr Ile
            180                 185                 190

Glu Gly Val Thr Asn Ser Thr Val Leu Ser Tyr Val Asn Asn Leu Asn
        195                 200                 205

Ala Asn Asp Phe Gly Ala Leu Ile Asp Leu Phe Ala Pro Asp Gly Ala
210                 215                 220

Leu Gln Pro Pro Phe Gln Lys Pro Ile Val Gly Arg Asp Ala Ile Thr
225                 230                 235                 240

Arg Phe Phe Asn Glu Glu Cys Gln Asn Leu Thr Leu Ile Pro Glu Arg
                245                 250                 255

Gly Ile Ser Glu Pro Val Glu Asp Gly Tyr Thr Gln Ile Lys Val Thr
            260                 265                 270

Gly Lys Val Gln Thr Pro Trp Phe Gly Ala Ala Val Gly Met Asn Ile
        275                 280                 285

Ala Trp Arg Phe Leu Leu Asn Pro Gln Gly Lys Ile Phe Phe Val Ala
290                 295                 300

Ile Asp Leu Leu Ala Ser Pro Lys Glu Leu Leu Asn Leu Met Arg
305                 310                 315

<210> SEQ ID NO 21
<211> LENGTH: 318
<212> TYPE: PRT
<213> ORGANISM: Synechococcus WH7805

<400> SEQUENCE: 21
```

-continued

```
Met Phe Thr Leu Asp Lys Ala Arg Gln Ile Phe Pro Glu Thr Met Thr
1               5                  10                  15

Ala Asp Ala Val Pro Ala Ile Thr Ala Arg Phe Lys Leu Leu Ser Pro
            20                  25                  30

Glu Asp Gln Leu Ala Leu Ile Trp Phe Ala Tyr Leu Glu Met Gly Gln
        35                  40                  45

Thr Ile Thr Val Ala Ala Pro Gly Ala Ala Arg Met Ala Leu Ala Lys
    50                  55                  60

Pro Thr Leu Asp Glu Ile Val Ala Met Ser Phe Asp Glu Gln Thr Lys
65                  70                  75                  80

Val Met Cys Asp Leu Ala Ala Lys Val Asn Ser Pro Val Ser Ser Arg
                85                  90                  95

Tyr Ala Phe Trp Ser Val Asn Val Lys Leu Cys Phe Trp Tyr Glu Leu
            100                 105                 110

Gly Glu Phe Met Arg Gln Gly Lys Val Ala Pro Ile Pro Gln Gly Tyr
        115                 120                 125

Lys Leu Ser Ala Asn Ala Thr Ser Val Leu Glu Ala Val Lys Lys Val
    130                 135                 140

Glu Gln Gly Gln Gln Ile Thr Leu Leu Arg Asn Phe Val Val Asp Met
145                 150                 155                 160

Gly Tyr Asp Pro Asp Val Asp Asp Ser Lys Val Val Ala Glu Pro Ile
                165                 170                 175

Val Ala Pro Thr Pro Glu Asp Gln Arg Glu Ile Phe Ile Pro Gly
            180                 185                 190

Val Leu Asn Gln Thr Ile Leu Ser Tyr Met Gln Leu Leu Asn Ala Asn
    195                 200                 205

Asp Phe Asp Gln Leu Ile Asp Leu Phe Leu Asp Asp Gly Ala Leu Gln
210                 215                 220

Pro Pro Phe Gln Arg Pro Ile Val Gly Arg Asp Ala Ile Leu Lys Phe
225                 230                 235                 240

Phe Lys Arg Asp Cys Gln Asn Leu Lys Leu Ile Pro Gln Gly Gly Phe
                245                 250                 255

Gly Glu Pro Ala Asp Ser Gly Phe Thr Gln Ile Lys Val Thr Gly Lys
            260                 265                 270

Val Gln Thr Pro Trp Phe Gly Arg Glu Val Gly Met Asn Val Ala Trp
    275                 280                 285

Arg Phe Leu Leu Asp Asp Asn Asn Lys Ile Tyr Phe Val Ala Ile Asp
290                 295                 300

Leu Leu Ala Ser Pro Ala Glu Leu Leu Lys Leu Gly Gly Lys
305                 310                 315

<210> SEQ ID NO 22
<211> LENGTH: 318
<212> TYPE: PRT
<213> ORGANISM: Synechococcus BL107

<400> SEQUENCE: 22

Met Tyr Thr Ile Asp Lys Ala Arg Gln Ile Phe Pro Asp Thr Gln Thr
1               5                  10                  15

Ala Asp Ala Val Pro Ala Ile Thr Ala Arg Phe Lys Leu Leu Ser Ala
            20                  25                  30

Glu Asp Gln Leu Ala Leu Ile Trp Phe Ala Tyr Leu Glu Met Gly Gln
        35                  40                  45

Thr Ile Thr Val Ala Ala Pro Gly Ala Ala Arg Met Ala Leu Ala Lys
    50                  55                  60
```

Pro Thr Leu Asp Glu Ile Val Ala Met Ser Phe Asp Glu Gln Thr Lys
65                  70                  75                  80

Val Met Cys Asp Leu Ala Ser Lys Ile Asn Ala Pro Ile Ser Thr Arg
                85                  90                  95

Tyr Ala Phe Trp Ser Ile Asn Val Lys Leu Gly Phe Trp Tyr Glu Leu
            100                 105                 110

Gly Glu Leu Met Arg Gly Gly Lys Val Ala Pro Ile Pro Pro Gly Tyr
        115                 120                 125

Lys Leu Ser Ala Asn Ala Ser Ser Val Leu Asp Ala Val Lys Lys Val
130                 135                 140

Glu Gln Gly Gln Gln Ile Ser Leu Leu Arg Asn Phe Val Ser Asp Met
145                 150                 155                 160

Gly Phe Asp Pro Asp Val Val Asp Asp Lys Leu Val Ala Glu Pro Ile
                165                 170                 175

Val Ala Pro Thr Pro Glu Ser Glu Arg Glu Lys Ile Phe Ile Pro Gly
            180                 185                 190

Val Leu Asn Gln Thr Ile Leu Ser Tyr Met Glu Leu Leu Asn Ser Asn
        195                 200                 205

Asp Phe Asp Gln Leu Ile Glu Leu Phe Leu Asp Asp Gly Ala Leu Gln
210                 215                 220

Pro Pro Phe Gln Arg Pro Ile Val Gly Arg Glu Ser Ile Leu Lys Phe
225                 230                 235                 240

Phe Arg Arg Asp Cys Gln Asn Leu Arg Leu Met Pro Gln Gly Gly Phe
                245                 250                 255

Gly Glu Pro Ala Asp Ser Gly Phe Asn Gln Ile Lys Val Thr Gly Lys
            260                 265                 270

Val Gln Thr Pro Trp Phe Gly Gln Glu Val Gly Met Asn Val Ala Trp
        275                 280                 285

Arg Phe Leu Leu Asp Glu Asn Asp Lys Ile Tyr Phe Val Ala Ile Asp
290                 295                 300

Leu Leu Ala Ser Pro Ala Glu Leu Leu Lys Leu Gly Gly Asn
305                 310                 315

<210> SEQ ID NO 23
<211> LENGTH: 318
<212> TYPE: PRT
<213> ORGANISM: Synechococcus RCC307

<400> SEQUENCE: 23

Met Tyr Thr Leu Asp Lys Ala Gln Gln Ile Phe Pro Glu Thr Leu Thr
1               5                   10                  15

Ala Asp Ala Val Pro Ala Ile Thr Ala Arg Phe Lys Gln Leu Ser Ala
            20                  25                  30

Glu Asp Gln Leu Ala Leu Ile Trp Phe Ala Tyr Leu Glu Met Gly Lys
        35                  40                  45

Thr Ile Thr Ile Ala Ala Pro Gly Ala Ala Arg Met Ala Leu Ala Glu
    50                  55                  60

Pro Thr Leu Lys Glu Ile Ala Gly Met Ser Ala Asp Glu Gln Thr Lys
65                  70                  75                  80

Val Met Cys Asp Leu Ala Ala Lys Ile Asn Ser Pro Ile Ser Asn Arg
                85                  90                  95

Tyr Ala Tyr Trp Ser Val Asn Val Lys Leu Gly Phe Trp Tyr Glu Leu
            100                 105                 110

Gly Glu Leu Met Arg Lys Gly Asp Val Ala Pro Ile Pro Pro Gly Tyr

```
              115                 120                 125
Ser Leu Ser Leu Asn Ala Asn Ser Val Leu Ala Ser Val Arg Lys Ala
        130                 135                 140

Glu Gln Gly Gln Gln Ile Thr Leu Leu Arg Asn Phe Val Val Asp Met
145                 150                 155                 160

Gly Phe Asp Pro Asn Ile Asp Asp Glu Lys Ile Gln Ser Glu Pro Ile
                165                 170                 175

Val Ala Pro Thr Pro Val Asp Gln Arg Glu Glu Ile Phe Ile Pro Gly
            180                 185                 190

Ile Leu Asn Gln Thr Ile Leu Asp Tyr Met Val Tyr Leu Asn Ala Asn
        195                 200                 205

Asp Phe Asp Gln Leu Ile Asp Leu Phe Leu Asp Gly Ala Leu Gln
    210                 215                 220

Pro Pro Phe Gln Arg Pro Ile Val Gly Arg Glu Ala Ile Leu Lys Phe
225                 230                 235                 240

Phe Arg Arg Asp Cys Gln Asn Leu Lys Leu Leu Pro Gln Gly Gly Tyr
                245                 250                 255

Gly Glu Pro Ala Glu Gly Gly Phe Asn Gln Ile Lys Val Thr Gly Lys
            260                 265                 270

Val Gln Thr Pro Trp Phe Gly Arg Glu Val Gly Met Asn Val Ala Trp
        275                 280                 285

Arg Phe Leu Leu Asp Glu Asn Asn Lys Ile Tyr Phe Val Ala Ile Asp
    290                 295                 300

Leu Leu Ala Ser Pro Ala Glu Leu Leu Lys Leu Gly Ala Lys
305                 310                 315

<210> SEQ ID NO 24
<211> LENGTH: 318
<212> TYPE: PRT
<213> ORGANISM: Synechococcus CC9902

<400> SEQUENCE: 24

Met Tyr Thr Ile Asp Lys Ala Arg Gln Ile Phe Pro Asp Thr Gln Thr
1               5                   10                  15

Ala Asp Ala Val Pro Ala Ile Thr Ala Arg Phe Lys Leu Leu Ser Ala
                20                  25                  30

Glu Asp Gln Leu Ala Leu Ile Trp Phe Ala Tyr Leu Glu Met Gly Gln
            35                  40                  45

Thr Ile Thr Val Ala Ala Pro Gly Ala Ala Arg Met Ala Leu Ala Lys
        50                  55                  60

Pro Thr Leu Asp Glu Ile Val Ala Leu Asn Phe Asp Glu Gln Thr Lys
65                  70                  75                  80

Val Met Cys Asp Leu Ala Ser Lys Ile Asn Ala Pro Ile Ser Thr Arg
                85                  90                  95

Tyr Ala Phe Trp Ser Ile Asn Val Lys Leu Gly Phe Trp Tyr Glu Leu
            100                 105                 110

Gly Glu Leu Met Arg Ala Gly Lys Val Ala Pro Ile Pro Pro Gly Tyr
        115                 120                 125

Lys Leu Ser Ala Asn Ala Ser Ser Val Leu Asp Ala Val Lys Lys Val
    130                 135                 140

Glu Gln Gly Gln Gln Ile Ser Leu Leu Arg Asn Phe Val Ser Asp Met
145                 150                 155                 160

Gly Phe Asp Pro Asp Val Val Asp Asp Gln Leu Val Ala Glu Pro Ile
                165                 170                 175
```

-continued

```
Val Ala Pro Thr Pro Val Glu Gln Arg Glu Lys Ile Phe Ile Pro Gly
            180             185             190

Val Leu Asn Gln Thr Ile Leu Ser Tyr Met Glu Leu Leu Asn Ser Asn
        195             200             205

Asp Phe Asp Gln Leu Ile Glu Leu Phe Leu Glu Asp Gly Ala Leu Gln
    210             215             220

Pro Pro Phe Gln Arg Pro Ile Val Gly Arg Glu Ala Ile Leu Lys Phe
225             230             235             240

Phe Arg Arg Asp Cys Gln Asn Leu Arg Leu Met Pro Gln Gly Gly Phe
                245             250             255

Gly Glu Pro Ala Asp Ser Gly Phe Asn Gln Ile Lys Val Thr Gly Lys
            260             265             270

Val Gln Thr Pro Trp Phe Gly Gln Glu Val Gly Met Asn Val Ala Trp
        275             280             285

Arg Phe Leu Leu Asp Glu Asn Asp Lys Ile Tyr Phe Val Ala Ile Asp
    290             295             300

Leu Leu Ala Ser Pro Ala Glu Leu Leu Lys Leu Gly Gly Asn
305             310             315
```

ENHANCEMENT OF BIOMASS PRODUCTION BY DISRUPTION OF LIGHT ENERGY DISSIPATION PATHWAYS

CROSS-REFERENCE TO RELATED APPLICATIONS

This application claims benefit of priority to U.S. provisional patent application 61/428,876 filed Dec. 31, 2010 entitled "Enhancement of Biomass Production by Disruption of Light Energy Dissipation Pathways which is hereby incorporated by reference in its entirety.

REFERENCE TO A SEQUENCE LISTING

This application contains references to amino acid sequences and/or nucleic acid sequences which have been submitted concurrently herewith as the sequence listing text file entitled "2010EM389 (PM0004) sequences_ST25.txt", file size 62.5 KiloBytes (KB), created on Dec. 20, 2011. The aforementioned sequence listing is hereby incorporated by reference in its entirety pursuant to 37 C.F.R. §1.52(e)(5).

TECHNICAL FIELD

The present invention relates, in some embodiments, to methods for culturing photosynthetic microorganisms for making various products. In some aspects, the invention relates to methods for producing biomass or biomolecules that include culturing a photosynthetic microorganism that comprises a disrupted Non-Photochemical Quenching (NPQ) process.

BACKGROUND

Photosynthesis is the conversion of light energy to chemical energy by biological systems. The first step of photosynthesis is the absorption of light by pigment-protein complexes. These complexes channel light energy to the photosynthetic reaction center, where light energy excites electrons that are transferred from pigment molecules through an electron transport chain that harvests the energy for biochemical reactions.

Microalgae, such as cyanobacteria, can be cultured photosynthetically for the production of various products, including proteins, peptides, amino acids, carbohydrates, isotopically labeled compounds, terpenoids, carotenoids, pigments, vitamins, and lipids, where light provides the energy for growth and biosynthesis of the algal products. Microalgal production systems can utilize open ponds (Ben-Amotz (1995) *J. Appl Phycol* 7: 65-68; Olaizola (2000) *J. Appl Phycol* 12: 499-506) or photobioreactors (Olaizola (2000) *J. Appl Phycol* 12: 499-506; Xu et al. (2009) *Eng. Life Sci* 9: 178-189; Lehr and Posten (2009) *Curr Opinion Biotechnol* 20: 280-285; US2009/0011492; WO2011/143619) where the energy for growth and production may be provided by natural or artificial light. In order to minimize production costs and maximize volumetric yield of photosynthetic microorganisms, it is desirable for the photosynthetic microorganisms to be grown in large volumes that reach high cell density. However, light penetration of an algal culture declines dramatically as culture depth and cell density increase. Active mixing of algal cultures propagated in a pond or photobioreactor allows the cultured algal cells to be exposed to higher levels of light intermittently when they are in proximity to the surface or light-facing boundary of a pond or photobioreactor. Actively mixed cultures cells experience some time periods of sub-optimal light, as well as some periods when the cells are at or close to the surface or perimeter of a pond or bioreactor where light may be super-saturating.

Algae typically use only a percentage of the solar radiation incident on a pond surface, and photosynthesis can be inhibited by excess solar radiation. When photosynthetic microorganisms are exposed to light of an intensity that is greater than the capacity for photosynthetic utilization, as may occur at the upper level of a pond or the periphery of a photobioreactor culture, the photosynthetic microorganisms may engage mechanisms for light energy dissipation to limit damage to the photosynthetic apparatus that might otherwise be caused by absorption of excess light energy.

Light energy can be lost from the pigment-protein complexes through mechanisms including fluorescence or by cell-regulated processes such as Non-Photochemical Quenching (NPQ). The qE component of NPQ is a protective mechanism that quenches singlet-excited chlorophylls (Chl) and harmlessly dissipates excess excitation energy as heat. These NPQ processes help to regulate and protect the photosynthetic apparatus from damage in environments in which light energy absorption exceeds the capacity for light utilization. In the absence of intrinsic NPQ mechanisms, such as energy dissipation mediated by carotenoids, photosynthetic organisms can incur photooxidative damage under water or nutrient limitation, low temperatures, and/or high light intensity (Demmig-Adams et al. (1996) *FASEB J.* 10: 403-412). In many cyanobacterial species, the Orange Carotenoid Protein binds the carotenoids zeaxanthin, echinenone, and/or hydroxyechinenone, and serves a photoprotective function in these species. *Synechocystis* cells having a mutant OCP gene had a greater decrease in photosynthetic activity than corresponding wild type cells in response to high light intensity (Wilson et al. *The Plant Cell* (2006) 18: 992-1007, and cyanobacterial species lacking an OCP gene were more photosynthetically impaired under high light conditions than species that have an OCP gene (Boulay et al. (2008) *Biochimica et Biophysica Acta* 1777: 1344-1354).

SUMMARY OF THE INVENTION

The invention provides a method of producing biomass or least one biomolecule comprising culturing a photosynthetic microorganism that comprises a disrupted Non-Photochemical Quenching (NPQ) process under conditions sufficient for the microorganism to proliferate in the culture, and isolating biomass or at least one biomolecule from the culture. In some embodiments, the amount of biomass or a biomolecule produced by the culture is at least 10% greater than the amount of biomass or a biomolecule produced by an identical culture of a microorganism identical in all respects except that it does not have a disrupted NPQ process. Additionally or alternately, the photosynthetic microorganism can be cultured phototrophically and/or under intermittent light conditions, optionally including natural light. The photosynthetic microorganism can be cultured in a culture system that includes active mixing during at least a portion of the time the culture is exposed to light (the light period). For example, the photosynthetic microorganism can be cultured in a pond or photobioreactor, such as a pond having a depth of at least 3 centimeters (cm), at least 5 cm, or at least 10 cm, or a photobioreactor having a light path of at least 3 cm, at least 5 cm, or at least 10 cm, where the culture is actively mixed. For example, the culture can be mixed using one or more powered paddle wheels, propellers, agitating devices, pumps, spargers, or injectors. Further additionally or alternately, the photosynthetic microorganism can be cultured in a volume of at least 20 liters of culture medium and/or can produce at least 0.1 g, for example at least 0.2 g or at least 0.3 g, of ash-free dry weight biomass per liter of culture.

A disrupted NPQ process in preferred embodiments comprises disrupted or reduced production of at least one carotenoid or at least one carotenoid binding protein in the photosynthetic microorganism, in which the microorganisms with a disrupted NPQ process exhibits less NPQ than does an control photosynthetic microorganism in which synthesis of a carotenoid or expression of a carotenoid binding protein is not disrupted. In some embodiments, disrupting the NPQ process can comprise disrupting the production of at least one carotenoid such as echinenone and/or hydroxyechinenone and/or disrupting the production of at least one carotenoid binding protein such as orange carotenoid protein (OCP). In such embodiments, disrupting the NPQ process can comprise reducing or inhibiting the expression of the OCP in the microorganism, e.g., by removing all or a portion of an OCP gene in the microorganism, by disrupting an OCP gene of a photosynthetic microorganism by insertional mutagenesis, and/or by reducing expression of an OCP gene in the microorganism, for example, by expression of antisense or ribozyme constructs.

The photosynthetic microorganism used in the methods provided herein can be any photosynthetic microorganism that includes an NPQ process, such as an NPQ process mediated by a carotenoid binding protein. Additionally or alternately, the photosynthetic microorganism can be a cyanobacterium. In some embodiments, the photosynthetic microorganism can be a cyanobacterium that includes a gene encoding an Orange Carotenoid Protein. As nonlimiting examples, the cyanobacterium can be a species of an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Crocosphaera, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* or *Xenococcus* genus. For example, the genetically engineered cyanobacterium can be a species of cyanobacteria that includes an endogenous gene encoding a protein that recruits to pfam PF09150 (the "Carot N" protein family) with a bit score of less than 25.0, and preferably with an e value of less than 0.01 or a protein having at least 40%, for example at least 45%, at least 50%, at least 55%, at least 60%, at least 65%, at least 70%, at least 75%, at least 80%, at least 85%, at least 90%, or at least 95%, amino acid sequence identity to SEQ ID NO:2. In some examples, the photosynthetic microorganism is a species of *Synechocystis, Arthrospira, Microcystis, Lyngbya, Nostoc, Anabaena, Synechococcus, Gloeobacter, Crocosphaera,* or *Thermosynechococcus*.

For example, the photosynthetic microorganism having a disrupted NPQ process can have attenuated expression of a carotenoid binding protein having at least 40%, for example at least 45%, at least 50%, for example at least 55%, at least 60%, at least 65%, at least 70%, at least 75%, at least 80%, at least 85%, at least 90%, or at least 95%, identity to SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. The photosynthetic microorganism that has a disrupted NPQ process (e.g., that has attenuated expression of an OCP gene) can produce at least one biomolecule such as a lipid, protein, peptide, amino acid, carbohydrate, isotopically labeled compound, vitamin, nucleotide, pigment, terpenoid, carotenoid, etc., or any combination thereof. For example, the microorganism can produce a lipid, such as a free fatty acid and/or a fatty acid derivative. The free fatty acid derivative can be, for example, a fatty aldehyde, a fatty alcohol, a fatty acid ester, a wax ester, an alkene, and/or an alkane. In some embodiments, the amount of free fatty acid or fatty acid derivative produced can be greater than the amount of free fatty acid or fatty acid derivative produced by a strain of photosynthetic microorganism identical in all respects except that it does not have a disrupted NPQ process that is grown under identical conditions.

In further aspects, the invention includes methods of producing a biomolecule, in which the methods comprise culturing a photosynthetic microorganism that comprises a disrupted Non-Photochemical Quenching (NPQ) process in which the photosynthetic microorganism includes at least one recombinant nucleic acid molecule that participates in or directs the biosynthesis the biomolecule under conditions in which the recombinant nucleic acid molecule is expressed, to produce the biomolecule. The microorganism can be cultured in a suitable culture medium, which in some examples can be a culture medium that does not included a substantial amount of a reduced carbon source, such that the cells are cultured photoautotrophically. Additionally, the culture medium can include inorganic carbon as substantially the sole source of carbon for production of the biomolecule. The photosynthetic microorganism can be cultured in pond or photobioreactor, for example a pond having a depth of at least 3 cm, or a photobioreactor having a light path of at least 3 cm, where preferably the culture undergoes active mixing. Additionally, the method can further include isolating the biomolecule from the microorganism, the culture medium, or both. The biomolecule can be any biomolecule, including, for example, a lipid, protein, carbohydrate, vitamin, peptide, amino acid, nucleotide, pigment, isotopically labeled compound, etc., or any combination thereof.

The invention also includes a photosynthetic microorganism having a disrupted NPQ process that includes at least one non-native gene for the production of a biomolecule such as a protein, lipid, pigment, terpenoid, carotenoid, vitamin, peptide, amino acid, or nucleotide. For example, a photosynthetic microorganism having a disrupted NPQ process can in some embodiments comprise one or more recombinant nucleic acid molecules that encode one or more proteins that participate in the biosynthesis of one or more lipids, such as, but not limited to, one or more free fatty acids and/or fatty acid derivatives. For example, the photosynthetic microorganism having a disrupted NPQ process can in some embodiments comprise one or more recombinant nucleic acid molecules that encode a thioesterase and/or a polypeptide having lipolytic activity, for example, a recombinant or exogenous nucleic acid molecule encoding one or more of the following: an acyl-ACP thioesterase; an acyl-CoA thioesterase; a hydroxybenzoyl-CoA thioesterase; a lipase that is a member of a pfam belonging to the AB Hydrolase pfam clan (CL0028); a lipase that includes a LipA domain identified as conserved protein domain COG1075, or is included in the protein family Pfam PF01674; s a lipase that includes a Lipase 3 domain identified as conserved protein domain COG3675, or is included in the protein family Pfam PF01764; a lipase that is included in the protein family Pfam PF07819; a lipase that is included in the protein family Pfam PF03583; a lipase that is included in the protein family Pfam PF00151; or a polypeptide having lipolytic activity that recruits to Pfam PF00561, Pfam PF02230, Pfam PF07859, Pfam PF08386, Pfam PF12695, Pfam PF12697, Pfam PF12715, or Pfam PF04083, or Pfam PF01425.

Additionally or alternately, a photosynthetic microorganism having a disrupted NPQ process can in some embodiments comprise one or more recombinant nucleic acid molecules encoding a protein that participates in or directs the synthesis of a lipid, such as but not limited to an acetyl-CoA carboxylase, a malonyl CoA: ACP transacylase, a beta-ketoacyl-ACP synthase, or a combination thereof. Further additionally or alternatively, a photosynthetic microorganism having a disrupted NPQ process can include one or more recombinant nucleic acid molecules encoding a protein that participates in the production of a fatty acid derivative, for example, one or more recombinant nucleic acid molecules encoding any combination of an acyl-CoA reductase, a carboxylic acid reductase, an acyl-ACP reductase, a fatty aldehyde reductase, a wax synthase, a fatty acid decarboxylase, a fatty aldehyde decarbonylase, and/or an acyl-CoA synthetase.

DETAILED DESCRIPTION

Figure 1:
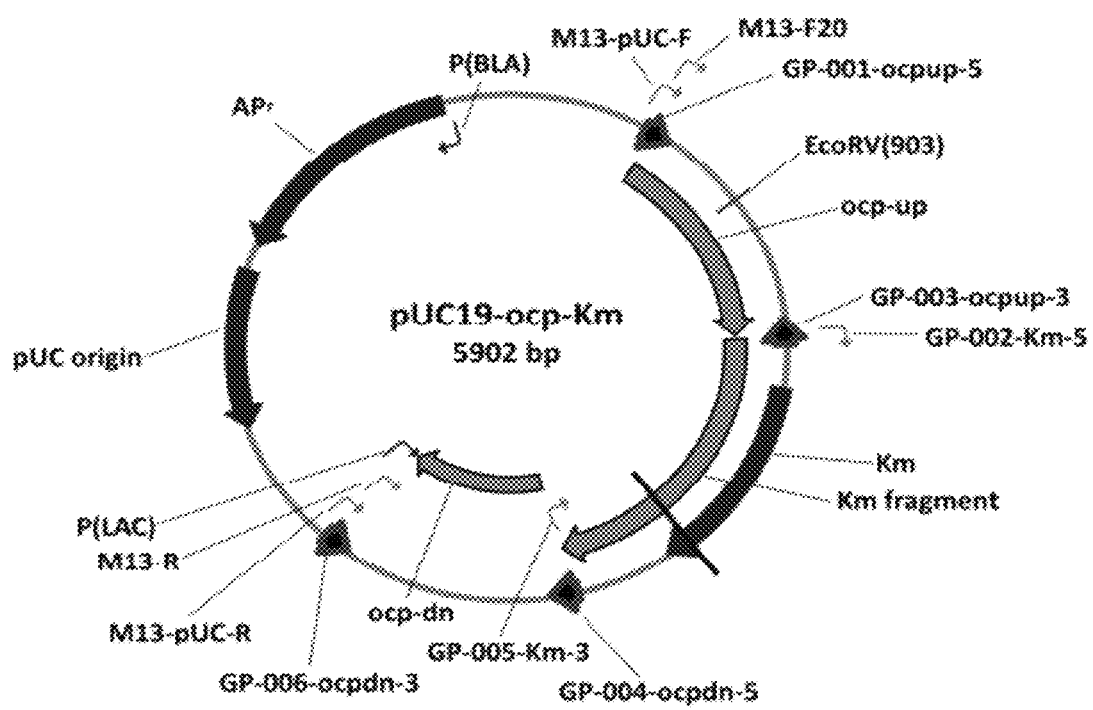
FIG. 1 shows a construct for knock-out of an OCP gene in *Synechocystis*.

As described herein, the present invention provides a method of producing biomass or at least one biomolecule comprising culturing a photosynthetic microorganism that comprises a disrupted Non-Photochemical Quenching (NPQ) process. The microorganism can be cultured photoautotrophically, for example, in a pond or photobioreactor, and can be cultured under intermittent light conditions, for example, under conditions in which the culture is actively mixed, such as by the use of one or more pumps, gas or liquid injectors, spargers, paddlewheels, propellers, or other mechanical devices for mixing, that can optionally be used in ponds or bioreactors that include one or more stationary structures that promote mixing or turbulence, and combinations thereof.

A biomolecule produced using the methods can be, without limitation, a protein, polymer, pigment, vitamin, peptide, amino acid, terpenoid, and/or lipid (e.g., monoacylglyceride, diacylglyceride, triacylglyceride, fatty acid, fatty acid derivative, or the like). Advantageously, a biomolecule can be recovered from the culture, such as from the culture medium, the microorganism, or a combination thereof. A "biomolecule" refers to any organic molecule that is produced by a living organism, including large polymeric molecules. Of particular relevance to the present invention are biomolecules that are useful, for example, as fuels, fuel additives, or fuel precursors, including fuel feedstocks, as well as biomolecules that are useful as chemical, lubricants, surfactants, and/or detergents. In some preferred embodiments, a biomolecule produced using the methods of the invention can be a monoglyceride, diglyceride, triglyceride, free fatty acid, fatty acid derivative, or combination thereof.

Alternatively or in addition, biomass can be recovered from the culture, and can optionally be used, for example, to extract, isolate, or purify one or more biomolecules or biomass components, or biomass itself can be a product of the culture where the recovered biomass can be used in further processes for example, for producing heat, energy, nutrients, syngas, one or more alcohols, etc. or can be used as a food supplement or animal feed or supplement. "Biomass" refers to organic matter stored from plants and other living things and can be regarded as an energy source, including, but not limited to, an energy source that can be converted to fuel or fuel feedstocks. Photosynthetic organisms perform photosynthesis, absorb carbon dioxide ($CO_2$), and convert it to biomass. When that biomass is burned, it is possible to recover heat energy. Alternatively, biomass can be added to food or animal feed, or can be converted to organic molecules (e.g., alcohols, through fermentation) that can be fuel or chemical feedstocks.

In some embodiments, the amount of biomass or of a biomolecule produced by the culture can be at least 10%, for example at least 15%, at least 20%, or at least 25%, greater than the amount of a biomolecule produced by an identical culture of a microorganism identical in all respects except that it does not have a disrupted NPQ process. Additionally or alternatively, the photosynthetic microorganism can be cultured phototrophically and/or under intermittent light conditions, e.g., in an actively mixed culture, optionally under natural light.

Further additionally or alternatively, the photosynthetic microorganism can be cultured in a volume of at least 20 liters, for example at least 50 liters, at least 100 liters, at least 200 liters, or at least 400 liters, of culture medium, and/or the photosynthetic microorganism can produce at least 0.1 g, for example at least 0.2 g or at least 0.3 g, of ash-free dry weight biomass per liter of culture.

A "disrupted NPQ process" preferably comprises disrupted production of at least one carotenoid and/or reduced expression of at least one carotenoid binding protein in the photosynthetic microorganism, in which the microorganisms with a disrupted NPQ process can advantageously exhibit less NPQ than does an control photosynthetic microorganism in which synthesis of a carotenoid and/or expression of a carotenoid binding protein is not disrupted. In some embodiments, disrupting the NPQ process can comprise disrupting the production of at least one carotenoid such as echinenone and/or hydroxyechinenone and/or disrupting the production of at least one carotenoid binding protein such as OCP, e.g., by reducing or inhibiting the expression of the OCP in the microorganism, such as by removing all or a portion of an OCP gene in the microorganism, by disrupting (such as, e.g., by insertional mutagenesis) an OCP gene of a photosynthetic microorganism, by the use of antisense constructs, and/or by otherwise reducing expression of an OCP gene in the microorganism.

Microorganisms

The genetically engineered microorganism in the present invention can be any photosynthetic microorganism, including without limitation, a cyanobacterium, alga, or the like. Photosynthetic microorganisms useful as host organisms can include, but are not limited to, any cyanobacteria that include an endogenous gene encoding an orange carotenoid protein (OCP). The microorganisms according to some embodiments of the present invention can include, but not limited to, the following genera of cyanobacteria: *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Crocosphaera, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus.* Cyanobacterial species that include one or more carotenoid binding proteins that participate in NPQ, such as for example a carotenoid binding protein that binds echinenone or hydroxyechinenone may be used in the methods provided herein, including but not limited to cyanobacterial species having an endogenous gene encoding a protein that recruits to pfam PF09150 (the "Carot N" protein family) with a bit score of less than 25.0, and preferably with an e value of less than 0.01 or that hasat least 40%, for example at least 45%, at least 50%, at least 55%, at least 60%, at least 65%, at least 70%, at least 75%, at least 80%, at least 85%, at least 90%, or at least 95%, amino acid sequence identity to SEQ ID NO:2. The microorganism can be, for example, a species of *Synechocystis, Arthrospira, Microcystis, Lyngbya, Nostoc, Anabaena, Synechococcus,* or *Gloeobacter.*

A number of cyanobacterial species are known and have been manipulated using molecular biological techniques, including the unicellular cyanobacteria *Synechocystis* sp. PCC6803 and *Synechococcus* elongates PCC7942, whose genomes have been completely sequenced.

In some embodiments, the cyanobacterial strain used in the methods of the invention can be a strain having a disrupted NPQ process and at least one recombinant nucleic acid molecule that encodes a protein that participates in and/or directs the production of at least one lipid, such as a fatty acid or fatty acid derivative (e.g., a fatty aldehyde, fatty alcohol, wax ester, alkane, and/or alkene).

Disruption of Non-Photochemical Quenching (NPQ) in Microorganisms

"NonPhotochemical Quenching" or "NPQ" is used herein to refer to an in vivo chlorophyll fluorescence quenching process that does not involve photochemistry (in which the energy of captured photons is transferred to chemical reactants, for example, components of the photosynthetic electron transport chain). NPQ can be observed by obtaining by measuring the maximal fluorescence (Fm) from dark adapted cells or chloroplasts stimulated with saturating light, and, after a series of light flashes observing a later maximal fluorescence (Fm') in response to a light flash, where the reduction in fluorescence from Fm to Fm' is due to NPQ.

In some photosynthetic microorganisms, NPQ can be induced from the activation of a carotenoid, such as echinenone and/or hydroxyechinenone, and/or the activity of a carotenoid binding protein, such as Orange Carotenoid Protein (OCP). As disclosed in the examples herein, disrupting the production of one or more carotenoids and/or a carotenoid binding protein, such as OCP, in a microorganism can increase the biomass production of the microorganism.

"Orange Carotenoid Protein" or "OCP" is a protein that binds the carotenoid hydroxyechinenone (e.g., 3'-hydroxyechinenone) and/or echinenone and contributes to nonphotochemical quenching. Nonlimiting examples of OCP include proteins that recruit to the protein family (Pfam) PF09150 with a bit score higher than the gathering cutoff for the family of 25.0, and preferable with an e value of less than 0.01, and proteins having the following Genbank Accession numbers and Gene Identifiers: ZP_03274607, GI:209526075 from *Arthrospira maxima* (SEQ ID NO:4); YP_001656905, GI:166364632 from *Microcystis aeruginosa maxima* (SEQ ID NO:5); ZP_01624422, GI:119493856 from *Lyngbya* sp. PCC 8106 (SEQ ID NO:6); YP_002379699, GI:218441370 from *Cyanothece* sp. PCC 7424 (SEQ ID NO:7); ZP_01726229, GI:126654695 from *Cyanothece* sp. CCY 0110 (SEQ ID NO:8); YP_001803065, GI:172036564 from *Cyanothece* sp. ATCC51142 (SEQ ID NO:9); YP_001868419, GI:186685223 from *Nostoc puctiforme* PCC73102 (SEQ ID NO:10); NP_487189, GI:17230641 from *Nostoc* sp PCC7120 (SEQ ID NO:11); YP_324343, GI:75910047 from *Anabaena variabilis* ATCC29413 (SEQ ID NO:12); ZP_07112967, GI:300868341 from *Oscillatoria* sp. PCC 6506 (SEQ ID NO:13); ZP_05028361, GI:254414596 from *Microcoleus chthonoplastes* PCC 7420 (SEQ ID NO:14); NP_926881, GI:37523504 (SEQ ID NO:15); ZP_01632514, GI:119513491 from *Nodularia spumigena* CCY9414 (SEQ ID NO:16); ZP_06309354, GI:282901429 from *Cylindrospermopsis raciborskii* CS-505 (SEQ ID NO:17); ZP_01080542, GI:87124694 from *Synechococcus* sp. RS9917 (SEQ ID NO:18); YP_001736034, GI:170079396 from *Synechococcus* sp. PCC 7002 (SEQ ID NO:19); ZP_06304225, GI:282896202 from *Raphidiopsis brookii* D9 (SEQ ID NO:20); ZP_01123774, GI:88808264 from *Synechococcus* sp. WH 7805 (SEQ ID NO:21); ZP_01468054, GI:116070785 from *Synechococcus* sp. BL107 (SEQ ID NO:22); YP_001228248, GI:148243091 from *Synechococcus* sp. RCC307 (SEQ ID NO:23); and YP_376983, GI:78184548 from *Synechococcus* sp. CC9902 (SEQ ID NO:24). OCPs can additionally or alternately include proteins having amino acid sequences that are at least 50%, for example at least 55%, at least 60%, at least 65%, at least 70%, at least 75%, at least 80%, at least 85%, at least 90%, or at least 95%, identical to the aforementioned proteins, where the reducing or disrupting expression of the protein in a photosynthetic microorganism reduces a nonphotochemical quenching process.

The invention provides methods of producing biomass or at least one biomolecule that can include culturing a cyanobacterium having a disrupted NPQ process in a culture volume of at least 20 liters, for example at least 50 liters, at least 100 liters, at least 200 liters, or at least 400 liters. NPQ can be reduced in the photosynthetic microorganism used in the methods by at least 5%, for example by at least 10%, at least 15%, or at least 20%, with respect to a photosynthetic microorganism identical in all respects except that it does not have a disrupted NPQ process. As provided in the Examples herein, photosynthetic microorganisms having a disrupted NPQ process can unexpectedly exhibit higher productivity than corresponding microorganisms having an intact (nondisrupted) NPQ process. Without limiting the invention to any particular mechanism, it is contemplated that in a production system in which cultures are mixed for optimal exposure to light, $CO_2$, and nutrients, the light environment for individual cells can change quickly as mixing occurs. Thus, although only a small portion of the time might be spent in conditions where light-intensity dependent damage might occur, NPQ may be activated and extend into periods of time when the cells are not experiencing excess light. The excessive duration of NPQ activation may reduce effectiveness of overall photosynthesis by preventing a cell from utilizing available light energy for photochemistry. Thus, although NPQ processes may be photoprotective in the natural state, in a mixed culture production system they may be disadvantageous.

Disruption of an NPQ process can be by disruption of the production of one or more carotenoids such as one or more ketocarotenoids, for example, echinenone and/or hydroxyechinenone, which can occur, e.g., by attenuating the expression of a gene on the biosynthetic pathway for these carotenoids. For example, production of a ketocarotenoid such as echinenone and/or hydroxyechinenone can be reduced and/or eliminated by mutation, downregulation, and/or insertional inactivation of a gene that encodes an enzyme that participates in the biosynthesis of beta-carotene, or that encodes an enzyme that participates in the conversion of beta-carotene to echinenone and/or hydroxyechinenone, such as for example, beta carotene hydroxylase (encoded by the crtR gene) and/or beta-carotene monoketolase (encoded by the crtO gene).

Preferably, disruption of the NPQ process does not include attenuating the expression of one or more proteins that may serve as a light absorbing antenna for photosynthetic light harvesting. For example, preferably disruption of the NPQ process does not include attenuating the expression of a chlorophyll-binding protein, such as, for example, one or more light harvesting chlorophyll binding proteins (LHCPs) that serve as an antenna for absorbing light energy for transfer to a photosynthetic reaction center.

Alternately or in addition, the expression of OCP can be disrupted by inhibiting or reducing expression of the OCP gene, and can include, for example, disrupting or deleting the OCP gene such that the OCP is not synthesized. For example, all or a portion of the OCP gene (and/or a gene encoding another carotenoid binding protein that participates in NPQ) can be deleted. In particular embodiments, when the OCP protein gene expression in a cyanobacterium is abolished or reduced, the biomass production of the cell can increase compared to a photosynthetic microorganism identical in all respects except that it does not have a disrupted OCP gene.

A gene encoding an OCP can be disrupted by replacement of all or a portion of the protein coding sequence or any part of the gene regulatory sequence of the OCP in the organism. Still further additionally or alternately, a gene can be attenuated by insertion of a sequence into the protein coding region and/or regulatory region of an OCP gene. Disruption by any such means can be performed, for example, by homologous recombination, which is well-established in cyanobacteria, among other organisms, or by using site-specific recombination in combination with homologous recombination. In preferred embodiments, gene disruption can result in a reduction in the amount of OCP produced by the engineered microorganism by at least 20%, for example by at least 30%, at least 40%, at least 50%, at least 60%, at least 70%, at least 80%, at least 90%, at least 95%, at least 97%, at least 99%, or about 100%, with respect to the same microorganism that does not include a disrupted OCP gene. In some preferred embodiments, the genetically engineered photosynthetic microorganism that has a disrupted OCP gene can have no detectable expression of the OCP.

In other examples, the expression of a gene encoding a polypeptide that functions in NPQ, such as an OCP gene, can be reduced or eliminated by expression of an antisense construct introduced into the photosynthetic microorganism. As used herein, an antisense construct refers particularly to a nucleic acid molecule that includes a sequence that encodes an antisense molecule, i.e., a ribonucleotide sequence having homology to at least a portion of the non-coding strand of a double stranded DNA molecule of a gene that encodes a protein (for example, at least 85%, at least 90%, at least 95%, at least 97%, at least 99%, or about 100% identical to at least a portion of the non-coding strand of a gene). Thus, an antisense molecule or "antisense RNA" can be complementary to at least a portion of the sequence of the coding strand of a double stranded DNA molecule that encodes a polypeptide. In the context of the present invention, an antisense RNA can be complementary to at least a portion of the sequence of the coding strand of a double stranded DNA molecule that encodes a polypeptide that functions in NPQ, e.g., an OCP gene. The antisense sequence may be complementary to protein-coding sequences of the targeted gene, or alternatively or in addition, the antisense sequence may be complementary wholly or in part to noncoding sequences specified on the transcribed strand of a DNA molecule encoding a protein, for example, a 5' untranslated region (UTR) and/or an intron. Antisense sequences are preferably at least 85% complementary, and more preferably at least 90% or at least 95% complementary to the target nucleic acid (gene) sequence. Expression of an antisense construct results in the production of an antisense RNA that has substantial or complete identity to at least a portion of a target gene. The sequence of the antisense RNA can correspond to the full length target gene (e.g., and OCP gene), or to a subsequence thereof. An antisense construct can include an antisense sequence of at least about twenty nucleotides, for example, at least about 25, at least about 30, at least about 40, at least about 50, at least about 100 or at least about 200 nucleotides having at least 85%, at least 90%, or preferably at least 95% identity to a sequence complementarity to a transcribed portion of a gene.

An antisense construct can additionally include one or more gene regulatory sequences operably linked to the antisense sequence, such as a promoter, where the promoter can be a constitutive or regulatable promoter. For example, a promoter that regulates expression of an antisense sequence can be an inducible promoter. Alternatively or in addition, the antisense construct can be integrated into the host microorganism's genome such that the antisense sequence is juxtaposed with, and operably linked to, an endogenous promoter of the host. In particular examples, the promoter can be an endogenous promoter that is active under the same conditions as the promoter that regulates expression of the endogenous gene encoding a polypeptide that functions in NPQ. In further examples, an antisense construct can include a copy of the same promoter that regulates the expression of the target gene in the host microorganism. Catalytic RNA molecules or ribozymes can also be used to inhibit expression of an OCP gene. For example, one or more ribozymes can be designed to specifically pair with the transcribed OCP-encoding RNA and cleave the phosphodiester backbone at a specific location to functionally inactivate the target RNA.

Further Modified Microorganisms

The present invention cultures of recombinant photosynthetic microorganisms having attenuated expression of a gene that encodes an enzyme for producing echinenone and/or hydroxyechinenone and/or having attenuated expression of a gene that encodes an OCP, can have reduced NPQ and/or can exhibit enhanced biomass production or biomolecule production with respect to a control microorganism. The recombinant photosynthetic microorganism with attenuated expression of a gene that functions in NPQ can, in some embodiments, also include other genetic modifications. Additional genetic modifications can include, without limitation, modifications that enhance the productivity or robustness of the strain. For example, one or more recombinant nucleic acid molecules can be introduced into the strain for directing the production of particular biomolecules, and/or for increasing or decreasing expression of endogenous genes that can directly or indirectly enhance the production of biomass or particular biomolecules in the modified strain.

For example, for the production of lipids, including fatty acids and/or fatty acid derivatives, the genetically engineered strain having reduced NPQ can be transformed with recombinant or heterologous thioesterase and/or lipase genes capable of producing free fatty acids from membrane lipids or storage lipids, e.g., phospholipids, triacylglycerol, diacylglycerol, monoacylglycerol, or the like, or combinations thereof.

Lipids are a class of molecules that are typically soluble in nonpolar solvents (such as ether and chloroform) and are relatively or completely insoluble in water. Lipid molecules have these properties, because they consist largely of hydrocarbon tails which are hydrophobic in nature. Examples of lipids include fatty acids (saturated and unsaturated); glycerides or glycerolipids (such as monoglycerides (monoacylglycerides), diglycerides (diacylglycerides), triglycerides (triacylglycerides) or neutral fats, phosphoglycerides or glycerophospholipids, or the like, or combinations thereof); non-glycerides (such as sphingolipids, sterol lipids including cholesterol and steroid hormones, prenol lipids including terpenoids, fatty alcohols, waxes, polyketides, or the like, or combinations thereof); and complex lipid derivatives (such as sugar—linked lipids, or glycolipids, protein-linked lipids, or the like, or a combination thereof). Fats are a subgroup of lipids and can include triacylglycerides.

Lipases are enzymes that catalyze the hydrolysis of ester bonds in glycerolipids, including, but not limited to, mono-, di-, and tri-acyl glycerols, as well as combinations thereof, to release free fatty acids and alcohols.

In some embodiments, the present invention relates to recombinant microorganisms transformed with at least one expression system including at least one lipase gene that operates to liberate fatty acids from one or more glycerolipids. In some embodiments of the present invention, the exogenous nucleic acid molecule encoding a thioesterase can include, without limitation, an acyl-ACP thioesterase, an acyl-CoA thioesterase, a hydroxylbenzoyl-CoA thioesterase, or a combination thereof.

The term "gene" is used broadly to refer to any segment of nucleic acid (typically DNA, but optionally RNA) associated with expression of a given RNA or protein. Thus, genes include sequences encoding expressed RNA (which can include polypeptide coding sequences) and, often, the regulatory sequences required for their expression. Genes can be obtained from a variety of sources, including cloning from a source of interest or synthesizing from known or predicted sequence information and may include sequences designed to have desired parameters.

"Pfam" is a large collection of protein domains and protein families maintained by the Pfam Consortium and available at several sponsored world wide web sites, including: pfam-.sanger.ac.uk/ (Welcome Trust, Sanger Institute); pfam.sbc-.su.se/(Stockholm Bioinformatics Center); pfam.janelia.org/ (Janelia Farm, Howard Hughes Medical Institute); pfam-.jouy.inra.fr/ (Institut national de la Recherche Agronomique); and pfam.ccbb.re.kr/. The latest release of Pfam is Pfam 26.0 (November 2011, 13672 families) based on the UniProt protein database release 15.6, a composite of Swiss-Prot release 57.6 and TrEMBL release 40.6. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment, whereas Pfam-B families are generated automatically from the non-redundant clusters of the latest release of the Automated Domain Decomposition algorithm (ADDA; Heger A, Holm L (2003) *J Mol Biol* 328(3):749-67). All identified sequences belonging to the family are then used to automatically generate a full alignment for the familiy (Sonnhammer et al. (1998) *Nucleic Acids Research* 26: 320-322; Bateman et al. (2000) *Nucleic Acids Research* 26: 263-266; Bateman et al. (2004) *Nucleic Acids Research* 32, Database Issue: D138-D141; Finn et al. (2006) *Nucleic Acids Research* Database Issue 34: D247-251; Finn et al. (2010) *Nucleic Acids Research* Database Issue 38: D211-222). By accessing the pfam database, for example, using any of the above-reference websites, protein sequences can be queried against the HMMs using HMMER homology search software (e.g., HMMER3, hmmer.janelia.org/). Significant matches that identify a queried protein as being in a pfam family (or as having a particular pfam domain) are those in which the bit score is greater than or equal to the gathering threshold for the Pfam domain. The gathering threshold for the pfam Acyl-ACP thioesterase family (PF01643) is 20.3. Expectation values (e values) can also be used as a criterion for inclusion of a queried protein in a pfam or for determining whether a queried protein has a particular pfam domain, where low e values (much less than 1.0, for example less than 0.1 or less than or equal to 0.01) represent low probabilities that a match is due to chance.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. et al., (1979) Principles of Protein Structure, Springer-Verlag). According to such analyses, groups of amino acids can be defined where amino acids within a group exchange preferentially with each other, and therefore resemble each other most in their impact on the overall protein structure (Schulz, G. E. et al., (1979) Principles of Protein Structure, Springer-Verlag). Examples of amino acid groups defined in this manner can include: a "charged/polar group," including Glu, Asp, Asn, Gln, Lys, Arg, and His; an "aromatic or cyclic group," including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into subgroups including: the "positively-charged sub-group," comprising Lys, Arg and His; the "negatively-charged sub-group," comprising Glu and Asp; and the "polar sub-group" comprising Asn and Gln. In another example, the aromatic or cyclic group can be sub-divided into sub-groups including: the "nitrogen ring sub-group," comprising Pro, His, and Trp; and the "phenyl sub-group" comprising Phe and Tyr. In another further example, the aliphatic group can be sub-divided into sub-groups including: the "large aliphatic non-polar sub-group," comprising Val, Leu, and Ile; the "aliphatic slightly-polar sub-group," comprising Met, Ser, Thr, and Cys; and the "small-residue sub-group," comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn such that a free —NH$_2$ can be maintained.

A "conservative variant" of a polypeptide is a polypeptide having one or more conservative amino acid substitutions with respect to the reference polypeptide, in which the activity, substrate affinity, binding affinity of the polypeptide does not substantially differ from that of the reference polypeptide. A substitution, insertion, or deletion can be said to adversely affect the protein when the altered sequence substantially inhibits a biological function associated with the protein.

Percent identity or homology with respect to such sequences is defined herein as the percentage of amino acid residues in the candidate sequence that are identical with the known peptides, after aligning the sequences and introducing gaps, if necessary, to achieve the maximum percent homology and not considering any conservative substitutions as part of the sequence identity. N-terminal, C-terminal, and/or internal deletions and/or insertions into the peptide sequence shall not be construed as affecting homology.

Homology or identity at the nucleotide or amino acid sequence level can be determined by BLAST (Basic Local Alignment Search Tool) analysis using the algorithm employed by the programs blastp, blastn, blastx, tblastn, and tblastx (Altschul et al. (1997), *Nucleic Acids Res.* 25, 3389-3402, and Karlin et al. (1990), *Proc. Natl. Acad. Sci. USA* 87, 2264-2268, both fully incorporated by reference), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul et al. (1994), *Nature Genetics* 6, 119-129, which is fully incorporated by reference. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff et al. (1992), Proc. Natl. Acad. Sci. USA 89, 10915-10919, fully incorporated by reference), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Another indication that two nucleic acid sequences have substantial homology is that the two molecules hybridize specifically to each other under stringent conditions. The phrase "hybridize specifically to" refers to the binding, duplexing, and/or hybridizing of a molecule only to a particular nucleotide sequence under stringent conditions, including when that sequence is present in a complex mixture (e.g., total cellular) of DNA and/or RNA. "Binds substantially" refers to complementary hybridization between a probe nucleic acid and a target nucleic acid and embraces minor mismatches that can be substantially accommodated by reducing the stringency of the hybridization media to achieve the desired detection of the target polynucleotide sequence. "Stringent hybridization conditions" and "stringent hybridization wash conditions", in the context of nucleic acid hybridization experiments such as Southern and northern hybridizations, are sequence dependent and are different under different environmental parameters.

Longer sequences can tend to hybridize specifically at higher temperatures. Generally, highly stringent hybridization and wash conditions can be selected to be about 5° C. lower than the thermal melting point (Tm) for the specific sequence at a defined ionic strength and pH. Typically, under "stringent conditions" a probe will generally hybridize to its target subsequence, but not to unrelated sequences.

The Tm is defined herein as the temperature (under defined ionic strength and pH) at which approximately 50% of the target sequence hybridizes to a perfectly matched probe. Very stringent conditions can be selected to be equal to the Tm for a particular probe. An example of stringent hybridization conditions for hybridization of complementary nucleic acids that have more than 100 complementary residues on a filter in a Southern or northern blot is about 50% formamide with about 1 mg of heparin at about 42° C., with the hybridization being carried out overnight (for about 6-16 hours). An example of highly stringent wash conditions includes about 0.15M NaCl at about 72° C. for about 15 minutes. An example of stringent wash conditions is a ~0.2×SSC wash at about 65° C. for about 15 minutes (see Sambrook, Molecular Cloning—A Laboratory Manual (2001), Cold Spring Harbor Laboratory Press). Often, a high stringency wash can be preceded by a low stringency wash to remove background probe signal. An example of a medium stringency wash for a duplex of, e.g., more than 100 nucleotides, is ~1×SSC at about 45° C. for about 15 minutes. An example of a low stringency wash for a duplex of, e.g., more than 100 nucleotides, is ~4-6×SSC at about 40° C. for about 15 minutes. For short probes (e.g., about 10 to 50 nucleotides), stringent conditions can typically involve salt concentrations of less than about 1.0 M Na$^+$ ion, typically from about 0.01 to about 1.0 M Na$^+$ ion, concentration (or other salts) at a pH of about 7.0 to about 8.3, with typical temperatures of at least about 30° C. Stringent conditions can additionally or alternately be achieved with the addition of destabilizing agents such as formamide. In general, a signal to noise ratio of about 2× (or higher) than that observed for an unrelated probe in the particular hybridization assay can indicate detection of a specific hybridization.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. (A descendent of a cell that was transformed with a nucleic acid molecule is also referred to as "transformed" if it has inherited the exogenous nucleic acid molecule). The exogenous gene may be from a different species (and so "heterologous"), or from the same species (and so "homologous"), relative to the cell being transformed. An "endogenous" nucleic acid molecule, gene, or protein is the organism's own nucleic acid molecule, gene, or protein as it occurs in, or is naturally produced by, the organism.

When referring to a gene regulatory sequence or to an auxiliary nucleic acid sequence used for maintaining or manipulating a gene sequence (e.g., a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter", even though the promoter may be derived from the same species (or, in some cases, the same organism) as the gene to which it is linked.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exo-nucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term recombinant, engineered, or genetically engineered refers to organisms that have been manipulated by introduction of an exogenous or recombinant nucleic acid sequence into the organism, and includes organisms having gene knockouts, targeted mutations and gene replacement, promoter replacement, deletion, or insertion, as well as organisms having exogenous genes that have been introduced into the organism. An exogenous or recombinant nucleic acid molecule can be integrated into the recombinant/genetically engineered organism's genome or in other instances may not be integrated into the recombinant/genetically engineered organism's genome.

The term "recombinant protein" as used herein refers to a protein produced by genetic engineering.

An "expression cassette", as used herein, refers to a gene encoding a protein or functional RNA (e.g., a tRNA, a microRNAs, a ribosomal RNA, etc.) operably linked to expression control sequences, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

When referring to a gene regulatory sequence or to an auxiliary nucleic acid sequence used for maintaining or manipulating a gene sequence (e.g., a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter", even though the promoter may be derived from the same species (or, in some cases, the same organism) as the gene to which it is linked.

As used herein "attenuated" means reduced in amount, degree, intensity, or strength. Attenuated gene expression may refer to a significantly reduced amount and/or rate of transcription of the gene in question, or of translation, folding, or assembly of the encoded protein.

A photosynthetic microorganism having a disrupted NPQ process that includes a recombinant gene encoding a protein that participates in the production of fatty acids, such as, for example, a recombinant thioesterase and/or lipase gene, can produce at least one free fatty acid, such as one or more of a $C_6$, $C_8$, $C_{10}$, $C_{12}$, $C_{14}$, $C_{16}$, $C_{18}$, $C_{20}$, $C_{22}$, and $C_{24}$ free fatty acid. In some embodiments, the microorganism can produce at least one free fatty acid during the growth of the culture, and/or can produce at least one free fatty acid in the absence of disruption or lysis of the cells. Recombinant thioesterase and/or lipase genes can optionally additionally be introduced into such photosynthetic microorganisms with a disrupted NPQ process, e.g., for the production of fatty acid derivatives.

Thioesterases useful in various aspects of the invention are enzymes that catalyze the cleavage of a fatty acid thioester. For example, "acyl-ACP thioesterase" is an enzyme that catalyzes the cleavage of a fatty acid from an acyl carrier protein (ACP). In some embodiments of the present invention, the exogenous nucleic acid molecule encoding a thioesterase can include, without limitation, an acyl-ACP thioesterase, an acyl-CoA thioesterase, and a hydroxylbenzoyl-CoA thioesterase.

For example, a microorganism for the production of free fatty acids in some embodiments can be transformed with a gene encoding an exogenous acyl-ACP thioesterase, such as a gene encoding a polypeptide that when queried against the pfam database, provides a match with Pfam PF01643 having a bit score of less than or equal to 20.3 (the gathering cut-off for PF01643). The exogenous acyl-ACP thioesterase gene can encode an acyl-ACP thioesterase from a higher plant species. Genes encoding acyl-ACP thioesterases derived from higher plants can include, without limitation, genes encoding acyl-ACP thioesterases from *Cuphea* species (e.g., *Cuphea carthagenensis, Cuphea wrightii* (e.g., AAC49784.1 GI:1336008), *Cuphea lanceolata* (e.g, CAA54060, GI495227), *Cuphea palustris*, (e.g., AAC49783.1 GI:1336006; AAC49179.1 GI:1215718); *Cuphea hookeriana* (e.g., AAC72882.1 GI:3859830; AAC49269.1 GI:1292906; AAC72881.1 GI:3859828; AAC72883.1 GI:3859832), *Cuphea calophylla* (e.g., ABB71580.1 GI:81361963)) or genes from other higher plant species. For example, a microorganism used in the methods and cultures disclosed herein can include a gene encoding an acyl-ACP thioesterase from species such as but not limited to, *Arabidopsis* (XP_002885681.1 GI:297835598; NP_172327.1 GI:15223236); *Arachis hypogaea* (e.g., AB038556.1 GI:133754634); *Brassica* species (e.g., CAA52069.1 GI:435011), *Camellia oleifera* ((e.g., ACQ57189.1 GI:229358082); *Cinnamonum camphorum* (e.g., AAC49151.1 GI:1143156); *Cocos nucifera; Glycine max* (e.g., ABD91726.1 GI:90192131); *Garcinia mangostana* (e.g., AAB51525.1 GI:1930081); *Gossypium hirsutum* (e.g., AAD01982.1 GI:4104242); *Helianthus annuus* (e.g., AAQ08226 GI:33325244); *Jatropha curcas* (e.g., ABU96744.1 GI:156900676); *Macadamia tetraphylla* (e.g., ADA79524.1 GI:282160399); *Elaeis oleifera* (e.g., AAM09524.1 GI:20067070); *Oryza sativa* (e.g., BAA83582.1 GI:5803272); *Populus tomentosa* (e.g., ABC47311.1 GI:83778888); *Umbellularia californica* (e.g., AAC49001.1 GI:595955); *Ulmus Americana* (e.g., AAB71731.1 GI:2459533); and *Zea mays* (ACG41291.1 GI:195643646), or any of those disclosed in U.S. Pat. No. 5,455,167; U.S. Pat. No. 5,654,495; and U.S. Pat. No. 5,455,167; all incorporated by reference herein in their entireties. Further included are acyl-ACP thioesterases from mosses (Bryophyta), such as, for example, *Physcomitrella patens*, (e.g., XP_001770108.1 GI:168035219). These examples are not limiting with regard to the types or specific examples of acyl-ACP thioesterase genes that can be used. Further included are acyl-ACP thioesterase genes from additional organisms, including, for example, prokaryotic organisms. Illustrative examples of prokaryotic acyl-ACP thioesterases that may be expressed by a microorganism useful in the methods and cultures provided herein include, but are not limited to acyl-ACP thioesterases from *Desulfovibrio desulfuricans* (e.g., Q312L1 GI:123552742); *Elusimicrobium minutum* (e.g., ACC98705 GI:186971720); *Carboxydothermus hydrogenoformans* (e.g., YP_359670 GI:78042959); *Clostridium thermocellum* (e.g., YP_001039461 GI:125975551); *Moorella thermoacetica* (e.g., YP_431036 GI:83591027); *Geobacter metallireducens* (e.g., YP_384688 GI:78222941); *Salinibacter ruber* (e.g., YP_444210 GI:83814393); *Microscilla marina* (e.g., EAY28464 123988858); *Parabacteroides distasonis* (e.g., YP_001303423 GI:150008680); *Enterococcus faecalis* (e.g., ZP_03949391 GI:227519342); *Lactobacillus plantarum* (e.g., YP_003062170 GI:254555753); *Leuconostoc mesenteroides* (e.g., YP_817783 GI:116617412); *Oenococcus oeni* (e.g., ZP_01544069 GI:118586629); *Mycobacterium smegmatis* (e.g., ABK74560 GI:118173664); *Mycobacterium vanbaalenii* (e.g., ABM11638 GI:119954633); *Rhodococcus erythropolis* (e.g., ZP_04385507 GI:229491686; *Rhodococcus opacus* (e.g., YP_002778825 GI:226361047), or any of those disclosed in the co-pending, commonly-assigned U.S. patent application 61/426,555 entitled "Prokaryotic Acyl-ACP Thioesterases for Producing Fatty Acids in Genetically Engineered Microorganisms", filed on Dec. 23, 2010, and which is incorporated herein by reference in its entirety.

A gene encoding an acyl-CoA thioesterase can optionally additionally be introduced into a host microorganism to generate free fatty acids. An acyl-CoA thioesterase gene transformed into a microorganism for the production of free fatty acids can be from a plant, animal, or microbial source. For example, a gene encoding the TesA or TesB thioesterase of *E. coli*, or a variant thereof, for example, an acyl-CoA thioesterase such as not limited to a variant as disclosed in PCT Publication No. WO 2010/075483, incorporated by reference herein in its entirety, can be introduced into a microorganism. Also included are genes encoding proteins that when queried against the Pfam database of protein families are identified as members of Pfam PF02551 (acyl-CoA thioesterase), where the bit score is equal to or greater than the gathering cut off (20.7).

Alternately or in addition, the microorganism can include one or more genes encoding an exogenous hydroxylbenzoyl-CoA thioesterase, for example an exogenous 4-hydroxybenzoate thioesterase or 4-chlorobenzoate thioesterase. Genes encoding hydroxybenzoyl thioesterases that may be useful in a microorganism for producing free fatty acids can include, for example, those disclosed in the co-pending, commonly-assigned U.S. patent application 61/426,568 entitled "Genetically Engineered Microorganisms Comprising 4-Hydroxybenzoyl-CoA Thioesterases and Methods of Using Same for Producing Free Fatty Acids and Fatty Acid Derivatives", filed on Dec. 23, 2010, and which is incorporated herein by reference in its entirety, 4-hydroxybenzoate thioesterases from *Bacillus* species and *Geobacillus* species, as well as 4-hydroxybenzoate thioesterases of *Acidiphilium, Bartonella, Rhodopseudomonas, Magnetospirillum, Burkholderia, Granulibacter, Rhizobium*, and *Labrenzia* species, or the like, or combinations thereof.

Further additionally or alternately, the recombinant microorganism can include those genetically engineered with exogenous or endogenous genes that encode polypeptides having lipolytic activity, such as, for example, lipases or esterases capable of producing free fatty acids from membrane lipids or storage lipids, e.g., phospholipids, glycolipids, triacylglycerols, diacylglycerols, monoacylglycerols, or the like, or combinations thereof. Lipases are enzymes that catalyze the hydrolysis of ester bonds in glycerolipids, including, but not limited to, mono-, di-, and tri-acyl glycerols, as well as combinations thereof, to release free fatty acids and alcohols.

The use of lipase genes in microorganisms used in the production of free fatty acids is disclosed in the co-pending, commonly-assigned U.S. patent application 61/426,624 entitled "Lipase-Mediated Production of Free Fatty Acids by Recombinant Microorganisms", filed on Dec. 23, 2010, and which is incorporated herein by reference in its entirety. The lipase gene can be a gene encoding any lipase, e.g., that liberates a fatty acid from a glycerolipid (including a monoglyceride, a diglyceride, a triglyceride, a phospholipid, a galactolipid, etc.). For example, a lipase gene can encode a polypeptide having lipase activity that is a member of the Pfam AB Hydrolase clan, CL0028, such as but not limited to, a lipase that is a member of Pfam 01674, Pfam 01764, Pfam 07819, Pfam 03583, and/or Pfam 00151. In some embodiments, an exogenous lipase gene introduced into a microorganism can encode a protein with an amino acid sequence having an E-value parameter of 0.01 or less when queried using the Pfam Profile HMM for any of Pfam PF01674, Pfam PF 01764, Pfam PF07819, Pfam PF03583, and/or Pfam PF00151. Additionally or alternately contemplated are recombinant microorganisms that are engineered to include gene regulatory sequences that induce or increase expression of an endogenous lipase gene. For example, a microorganism can be engineered such that a heterologous promoter is inserted upstream of a coding region of an endogenous lipase gene. The heterologous promoter can replace an endogenous promoter and/or can be inserted upstream or downstream of the endogenous promoter that regulates expression of the endogenous lipase gene, for example using homologous recombination or site-specific recombination. The heterologous promoter can be a constitutive promoter or an inducible promoter that increases expression of the endogenous lipase gene.

Still further additionally or alternately, the microorganism can include nucleic acid molecules encoding variants of the above-listed acyl-ACP thioesterases, acyl-CoA thioesterases, hydroxylbenzoyl-CoA thioesterases, or lipases, in which the variants have at least 80%, for example at least 85%, at least 90%, or at least 95%, identity to the amino acid sequences accessed by the provided or referenced Genbank Accession Numbers, in which the variants have at least the level of activity (e.g., thioesterase or lipase activity) as the reference sequence.

In some embodiments, the present invention relates to a recombinant microorganism having a disrupted NPQ process, for example, a recombinant photosynthetic microorganism that has reduced expression of a gene on the biosynthetic pathway or a gene having reduced expression of OCP, that exhibits disrupted NPQ, that includes at least one recombinant expression system for at least one thioesterase gene and/or at least one lipase gene that operates to liberate and/or release fatty acids. A "free fatty acid", as used herein, is meant to refer to a non-esterified acyl moiety that is substantially unassociated, e.g., with an enzyme and/or protein, within or outside an organism (e.g., globular and/or micellular storage within an organism, without esterification, can still qualify as a free fatty acid). Thus, a free fatty acid according to the present invention need not necessarily be a strict acid or be structurally "free", but a free fatty acid specifically does not include an acyl moiety whose carboxylate oxygen is covalently linked to any other moiety other than a hydrogen atom (meaning that fatty acid esters are specifically not included in free fatty acids. However, a free fatty acid can advantageously include an acyl moiety containing at least four carbons (preferably at least 6 carbons, for example at least 8 carbons), in which the acyl moiety (i) is covalently linked to a hydrogen atom, (ii) has an ionic charge, to which a counterion can be associated (even if loosely and/or solvent-separated), and/or (iii) is associated, but not covalently bonded to another moiety that is relatively easily transformable into the corresponding acid form or the corresponding ionic form (e.g., through hydrogen-bonding or the like). Non-limiting examples of counterions can include metals salts (such as calcium, magnesium, sodium, potassium, aluminum, iron, and the like, and combinations thereof), other inorganic ions (such as ammonium, mono-, di-, tri-, and tetra-alkylammonium, sulfonium, phosphonium, and the like, and combinations thereof), organic ions (such as carbocations), and the like, and combinations thereof.

Other Modifications for Producing Free Fatty Acids and/or Fatty Acid Derivatives Additionally or alternately to providing an expression system for one or more exogenous genes, such as thioesterase and lipase genes, further modifications in the microorganism may be made. For example, in addition to having an exogenous thioesterase gene and/or a recombinant lipase gene, a microorganism used in the methods herein can additionally or alternately include microorganisms having at least one additional exogenous nucleic acid molecule that encodes a polypeptide that participates in the synthesis of a fatty acid.

For example, a transgenic microorganism for the production of one or more fatty acids can include an exogenous gene encoding an acetyl-CoA carboxylase, a malonyl CoA: ACP transacylase, or a beta-ketoacyl-ACP synthase.

The present invention also provides recombinant microorganisms that further include at least one endogenous gene that is attenuated or disrupted. Such an endogenous gene that can be attenuated or disrupted in the recombinant microorganism includes, but not limited to, acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, and the like, and combinations thereof.

Further additionally or alternately, the microorganism can be modified such that one or more genes that encode beta-oxidation pathway enzymes have been inactivated and/or downregulated, and/or such that the enzymes themselves that are operative on such beta-oxidation pathways may be inhibited. This could prevent the degradation of fatty acids released from acyl-ACPs, thus enhancing the yield of secreted fatty acids. In cases where the desired products are medium-chain fatty acids, the inactivation and/or downregulation of genes that encode acyl-CoA synthetase and/or acyl-CoA oxidase enzymes that preferentially use these chain lengths as substrates could be beneficial. Mutations in the genes encoding medium-chain-specific acyl-CoA synthetase and/or medium-chain-specific acyl-CoA oxidase enzymes, such that the activity of the enzymes could be diminished, may additionally or alternately be effective in increasing the yield of produced and/or released fatty acids. An additional modification can inactivate and/or downregulate the acyl-ACP synthetase gene and/or can inactivate and/or inhibit the encoded protein. Mutations in the genes can be introduced either by recombinant or non-recombinant methods. These enzymes and their genes are known and may be targeted specifically by disruption, deletion, generation of antisense sequences, generation of ribozymes, and/or other recombinant approaches known to the practitioner. Inactivation of the genes can additionally or alternately be accomplished by random mutation techniques such as exposure to UV and/or chemical mutagens, and the resulting cells can be screened for successful mutants. The proteins themselves can be inhibited by intracellular generation of appropriate antibodies, intracellular generation of peptide inhibitors, or the like, or some combination thereof.

Still further additionally or alternately, the photosynthetic microorganism can be modified such that one or more genes that encode storage carbohydrate and/or polyhydroxyalkanoate (PHA) biosynthesis pathway enzymes can be inactivated or downregulated, and/or such that the enzymes themselves that are operative on such pathways are inhibited. Examples include, but not limited to, enzymes involved in glycogen, starch, or chrysolaminarin synthesis, including glucan synthases and branching enzymes. Other examples include enzymes involved in PHA biosynthesis such as acetoacetyl-CoA synthase and PHA synthase.

Further Modifications for Producing Fatty Acid Derivatives

Additionally or alternately to providing an expression system for one or more appropriate recombinant genes, such as lipase genes, further modifications in the microorganism may be made. For example, in some embodiments, the genetically engineered photosynthetic microorganism having a disrupted NPQ process can produce a fatty aldehyde and can include one or more nucleic acid molecules encoding an exogenous acyl-CoA reductase, carboxylic acid reductase, and/or acyl-ACP reductase. Additionally or alternately, the genetically engineered photosynthetic microorganism can produce a fatty alcohol and can include at least one nucleic acid molecule encoding an exogenous acyl-CoA reductase, carboxylic acid reductase, or acyl-ACP reductase or at least one exogenous fatty aldehyde reductase. Alternatively or in addition, the genetically engineered photosynthetic microorganism of the described invention can produce a wax ester and can include one or more nucleic acid molecules encoding an exogenous acyl-CoA reductase, carboxylic acid reductase, or acyl-ACP reductase, and an exogenous wax synthase. Wax esters include an A chain and a B chain linked through an ester bond, one or both of which can be derived from a fatty acid generated by the exogenous 4-hydroxybenzoyl-CoA thioesterase. Wax esters produced by a photosynthetic microorganism that includes a nucleic acid molecule encoding an exogenous 4-hydroxybenzoyl-CoA thioesterase therefore can have A+B chain lengths of, for example, 16 to 36 carbons, 16 to 32 carbons, or 24 to 32 carbons.

In some embodiments, the photosynthetic microorganism having a disrupted NPQ process can produce an alkane or alkene and can include at least one nucleic acid molecule encoding an exogenous fatty acid decarboxylase or an exogenous fatty aldehyde decarbonylase, or additionally can include at least one exogenous nucleic acid molecule encoding an exogenous acyl-CoA reductase, carboxylic acid reductase, or acyl-ACP reductase. Alkanes and alkenes produced by a photosynthetic microorganism that includes a nucleic acid molecule encoding an exogenous 4-hydroxybenzoyl-CoA thioesterase can, for example, have chain lengths of 7, 9, 11, 13, 15, 17, 19, 21, and/or 23 carbons, for example, chain lengths of 7, 9, 11, 13, 15, and/or 17 carbons, or chain lengths of 7, 9, 11, 13, and/or 15 carbons, or chain lengths of 11, 13, and/or 15 carbons.

Additionally, a genetically engineered photosynthetic microorganism that produces a fatty alcohol, fatty aldehyde, wax ester, alkane, or alkene may optionally include a nucleic acid molecule encoding an acyl-CoA synthetase.

Additionally or alternatively to the embodiments provided hereinabove, the present invention also provides recombinant microorganisms having a disrupted NPQ process that further include at least one endogenous gene that is attenuated or disrupted to enhance production of a biomolecule such as a fatty acid or fatty acid derivative. Such an endogenous gene that can be attenuated or disrupted in the recombinant microorganism includes, but not limited to, acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, and the like, and combinations thereof.

Further additionally or alternatively, the microorganism can be modified such that one or more genes that encode beta-oxidation pathway enzymes have been inactivated or downregulated, and/or such that the enzymes themselves that are operative on such beta-oxidation pathways may be inhibited. This would prevent the degradation of fatty acids released from acyl-ACPs, thus enhancing the yield of secreted fatty acids. Mutations in a gene encoding acyl-CoA synthetase and/or acyl-CoA oxidase enzyme, such that the activity of one or more of these enzymes could be diminished, would additionally or alternatively be effective in increasing the yield of produced and/or released fatty acids. An additional or alternative modification can inactivate or downregulate the acyl-ACP synthetase gene and/or can inactivate or inhibit the encoded protein. Mutations in a gene can be introduced either by recombinant or non-recombinant methods. These enzymes and their genes are known and may be targeted specifically by disruption, deletion, generation of antisense sequences, generation of ribozymes, RNAi, and/or other recombinant approaches known to the practitioner. Inactivation of the genes can additionally or alternately be accomplished by random mutation techniques such as exposure to UV and/or chemical mutagens, and the resulting cells can be screened for successful mutants. The proteins themselves can be inhibited by intracellular generation of appropriate antibodies, intracellular generation of peptide inhibitors, or the like, or some combination thereof.

Again still further additionally or alternately, the photosynthetic microorganism having a disrupted NPQ process can be modified such that one or more genes that encode storage carbohydrate and/or polyhydroxyalkanoate (PHA) biosynthesis pathway enzymes can be inactivated or downregulated, and/or such that the enzymes themselves that are operative on such pathways are inhibited. Examples include, but not limited to, enzymes involved in glycogen, starch, or chrysolaminarin synthesis, including glucan synthases and branching enzymes. Other examples include enzymes involved in PHA biosynthesis such as acetoacetyl-CoA synthase and PHA synthase.

Expression Systems

The recombinant microorganisms of the present invention, in some embodiments, are transformed with exogenous genes by the introduction of appropriate expression vectors.

"Expression vector" or "expression construct" refers to a nucleic acid that has been generated via human intervention, including by recombinant means and/or direct chemical synthesis, with a series of specified nucleic acid elements that permit transcription and/or translation of a particular nucleic acid in a host cell. The expression vector can be a plasmid, a part of a plasmid, a viral construct, a nucleic acid fragment, or the like, or a combination thereof. Typically, the expression vector can include a nucleic acid to be transcribed operably linked to a promoter in an "expression cassette". Moreover, "inducible promoter" refers a promoter that mediates transcription of an operably linked gene in response to a particular stimulus. "Operable linkage" is a functional linkage between two nucleic acid sequences, such as a control sequence (typically a promoter) and the linked sequence (typically a sequence that encodes a protein and/or other biomolecule, also called a coding sequence). A promoter is in operable linkage with an exogenous gene if it can mediate transcription of the gene.

Vectors can be introduced into prokaryotic and eukaryotic cells via conventional transformation and/or transfection techniques. The terms "transformation" and "transfection", conjugation and transduction, as used in the present context, are intended to comprise a multiplicity of methods known to those skilled in the art for the introduction of foreign nucleic acid (for example, exogenous DNA) into a host cell, including calcium phosphate and/or calcium chloride co-precipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g., can be found in Molecular Cloning—A Laboratory Manual (2001), Cold Spring Harbor Laboratory Press.

For example, algae and photosynthetic bacteria can be transformed by any suitable methods, including, as non-limiting examples, natural DNA uptake (Chung et al. (1998) *FEMS Microbiol. Lett.* 164: 353-361; Frigaard et al. (2004) *Methods Mol. Biol.* 274: 325-40; Zang et al. (2007) *J. Microbiol.* 45: 241-245), conjugation, transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* 62: 503-9), biolistics (Dawson et al. (1997) *Curr. Microbiol.* 35: 356-62; Hallmann et al. (1997) 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017), electroporation (Kjaerulff et al. (1994)*Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, incubation with DNA in the presence of or after pre-treatment with any of poly(amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, and/or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365), or the like, or combinations thereof. *Agrobacterium*-mediated transformation can additionally or alternately be performed on algal cells, for example after removing or wounding the algal cell wall (e.g., PCT Publication No. WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; PCT Publication No. WO 2003/091413; PCT Publication No. WO 2005/005643; and PCT Publication No. WO 2007/133558, all incorporated herein by reference in their entireties).

For optimal expression of a recombinant protein, in many instances it can be beneficial to employ coding sequences that produce mRNA with codons preferentially used by the host cell to be transformed. Thus, for an enhanced expression of transgenes, the codon usage of the transgene can be matched with the specific codon bias of the organism in which the transgene is desired to be expressed. For example, methods of recoding genes for expression in microalgae are described in U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some embodiments, only a portion of the codons can be changed to reflect a preferred codon usage of a host microorganism, and in some embodiments, one or more codons can be changed to codons that are not necessarily the most preferred codon of the host microorganism encoding a particular amino acid. Additional information for codon optimization is available, e.g., at the codon usage database of GenBank. Accordingly, the present invention also provides, in some embodiments, for recombinant microorganisms transformed with an isolated nucleic acid molecule including a nucleic acid sequence that is codon-optimized for expression in the recombinant microorganism.

In some embodiments, the present invention additionally or alternately provides recombinant microorganisms transformed with an isolated nucleic acid molecule including a nucleic acid sequence operably linked to one or more expression control elements. For example, in some preferred embodiments of the invention, a gene (such as a gene as disclosed herein), can be cloned into an expression vector for transformation into a fungus, an alga, or a photosynthetic or non-photosynthetic bacterium. The vector can include sequences that promote expression of the transgene of interest (e.g., an exogenous lipase gene), such as a promoter, and may optionally include, for expression in eukaryotic cells, an intron sequence, a sequence having a polyadenylation signal, or the like, or combinations thereof. Alternatively, if the vector does not contain a promoter in operable linkage with the gene of interest, the gene can be transformed into the cells such that it becomes operably linked to an endogenous promoter by homologous recombination, site specific integration, and/or vector integration.

Additionally or alternately, the vector introduced in to a microorganism can include a promoter or transcriptional enhancer sequence not in operable linkage with a gene of interest, where the promoter or enhancer is positioned next to one or more sequences for directing the promoter to the chromosomal locus of a gene for producing fatty acids (e.g., an endogenous lipase gene). For example, sequences for homologous recombination or site-specific recombination can be engineered to flank a transcriptional regulatory sequence in a transformation vector, such that following transformation into the cells the regulatory sequence integrates into the host chromosome becomes operably linked to an endogenous gene by homologous recombination, site specific integration, and/or vector integration.

Vectors designed for expression of a gene in microalgae can alternatively or in addition include a promoter active in microalgae operably linked to the exogenous gene being introduced. A variety of gene promoters and terminators that function in green algae can be utilized in expression vectors, including, but not limited to, promoters and/or terminators from *Chlamydomonas* and other algae (see, for example, Abe et al. (2008) *Plant Cell Physiol,* 49: 625-632), promoters and/or terminators from viruses, synthetic promoters and/or terminators, or the like, or combinations thereof.

For transformation of diatoms, a variety of gene promoters that function in diatoms can be utilized in these expression vectors, including, but not limited to: 1) promoters from *Thalassiosira* and other heterokont algae, promoters from viruses, synthetic promoters, or the like, or combinations thereof. Promoters from *Thalassiosira pseudonana* and/or *Phaeodactylum tricornutum* that could be suitable for use in expression vectors can include an alpha-tubulin promoter, a beta-tubulin promoter, an actin promoter, or a combination thereof. The terminators associated with these genes, other diatom genes, and/or particular heterologous genes can be used to stop transcription and/or provide the appropriate signal, e.g., for polyadenylation.

In some instances, it can be advantageous to express an antisense molecule, or a gene encoding an exogenous and/or heterologous enzyme, such as but not limited to a lipase, at a certain point during the growth of the transgenic host, e.g., to minimize any deleterious effects on the growth of the transgenic organism and/or to maximize production of the fatty acid product of interest. In such instances, one or more exogenous genes introduced into the transgenic organism can be operably linked to an inducible promoter. The promoter can be, for example, a lac promoter, a tet promoter (e.g., U.S. Pat. No. 5,851,796), a hybrid promoter that includes either or both of portions of a tet or lac promoter, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (U.S. Pat. No. 5,750,385, U.S. Pat. No. 5,639,952) or temperature (U.S. Pat. No. 5,447,858; Abe et al. (2008) Plant Cell Physiol. 49: 625-632; Shroda et al. (2000) Plant J. 21: 121-131). The foregoing list is exemplary and not limiting. The promoter sequences can be from any organism, provided that they are functional in the host organism. Inducible promoters, as used in the constructs of the present invention, can use one or more portions or domains of the aforementioned promoters and/or other inducible promoters fused to at least a portion of a different promoter that can operate in the host organism, e.g., to confer inducibility on a promoter that operates in the host species.

For transformation of cyanobacteria, a variety of promoters that function in cyanobacteria can be utilized, including, but not limited to, the lac, tac, and trc promoters, as well as derivatives that are also inducible by the addition of isopropyl β-D-1-thiogalactopyranoside (IPTG) such as the trcY or trcE promoter. Other promoters that may find use in the invention include promoters that are naturally associated with transposon- or bacterial chromosome-borne antibiotic resistance genes (e.g., neomycin phosphotransferase, chloramphenicol acetyltransferase, spectinomycin adenyltransferase, or the like, or combinations thereof), promoters associated with various heterologous bacterial and native cyanobacterial genes, promoters from viruses and phages, synthetic promoters, or the like, or combinations thereof. Promoters isolated from cyanobacteria that can be used can include but are not limited to the following: nrs (nickel-inducible), secA (secretion; controlled by the redox state of the cell), rbc (Rubisco operon), psaAB (PS I reaction center proteins; light regulated), psbA (D1 protein of PSII; light-inducible), and the like, and combinations thereof. In some embodiments, the promoters are regulated by nitrogen compounds, such as, for example, nar, ntc, nir or nrt promoters. In some embodiments, the promoters are regulated by phosphate (e.g., pho or pst promoters) or metals (e.g., the nrs promoter (Liu and Curtis (2009) *Proc Natl Acad Sciences USA* 106: 21550-21554), or the petE promoter (Buikema and Haselkorn (2001) *Proc Natl Acad Sciences USA* 98: 2729-2734)). Inducible promoters, as used in the constructs of the present invention, can use one or more portions or domains of the aforementioned promoters and/or other inducible promoters fused to at least a portion of a different promoter that can operate in the host organism, e.g., to confer inducibility on a promoter that operates in the host species.

Likewise, a wide variety of transcriptional terminators can be used for expression vector construction. Examples of possible terminators can include, but are not limited to, psbA, psaAB, rbc, secA, T7 coat protein, and the like, and combinations thereof.

Transformation vectors can additionally or alternately include a selectable marker, such as but not limited to a drug resistance gene, an herbicide resistance gene, a metabolic enzyme and/or factor required for survival of the host (for example, an auxotrophic marker), or the like, or a combination thereof. Transformed cells can be optionally selected based upon the ability to grow in the presence of the antibiotic and/or other selectable marker under conditions in which cells lacking the resistance cassette or auxotrophic marker could not grow. Further additionally or alternatively, a non-selectable marker may be present on a vector, such as a gene encoding a fluorescent protein or enzyme that generates a detectable reaction product.

Expression vectors can be introduced into the cyanobacterial strains by standard methods, including, but not limited to, natural DNA uptake, conjugation, electroporation, particle bombardment, abrasion with glass beads, SiC fibers, or other particles, or the like, or combinations thereof. The vectors can be: (1) targeted for integration into the cyanobacterial chromosome, e.g., by including flanking sequences that enable homologous recombination into the chromosome; (2) targeted for integration into endogenous cyanobacterial plasmids, e.g., by including flanking sequences that enable homologous recombination into the endogenous plasmids; and/or (3) designed such that the expression vectors replicate within the chosen host.

According to some preferable embodiments, the present invention can involve recombinant microorganisms transformed with an isolated nucleic acid molecule including a nucleic acid sequence that is under control of a heterologous promoter. In such embodiments, the heterologous promoter can be an inducible promoter, such as an isopropyl β-D-1-thiogalactopyranoside (IPTG)-inducible promoter, for example, a lac, tac, and/or trc promoter, such as trcE and/or trcY.

Methods of Producing Biomass or One or More Biomolecules

The invention encompasses methods of producing biomass or at least one biomolecule by culturing the photosynthetic microorganisms described herein and isolating biomass or at least one biomolecule from the culture. The photosynthetic microorganisms used for production of biomass or a biomolecule have a disrupted NPQ process, for example, the production microorganism may have reduced production of a carotenoid or a carotenoid-binding protein. The microorganism used in the methods may be, in certain examples, a cyanobacterium with attenuated expression of an OCP. The photosynthetic microorganism can be cultured as an actively mixed culture, for example in a pond or photobioreactor. For example, the photosynthetic microorganism having a disrupted NPQ process can be cultured in a pond having a depth of at least 3 cm, at least 5 cm, or at least 10 cm, or a photobioreactor having a light path of at least 3 cm, at least 5 cm, or at least 10 cm, and the pond or bioreactor can include at least one active mixing device, such as a paddlewheel, pump, propeller, fluid injection system, sparger, or any combination thereof, optionally in combination with at least one passive mixing device.

The amount of biomass or a biomolecule produced by the culture according to some embodiments of the present invention can at least about 10%, for example at least about 20%, at least about 25%, or at least about 30% more than the amount of biomass or of a biomolecule produced by an identical culture of a microorganism identical in all respects except that it does not have a disrupted NPQ process.

In some embodiments of the present invention, the photosynthetic microorganisms can be cultured in an open pond where the culture is actively mixed, for example, by means of a paddle wheel, drag board, one or more pumps, including mechanical and air lift pumps, one or more propellers, paddles, or blades, gas spargers, or one or more streams or jets of liquid or gas and may additionally include one or more stationary structures within the pond or along one or more of its walls that promotes mixing or turbulence. As used herein "pond" means any open body of water, whether naturally-occurring or man-made, including ponds, canals, trenches, lagoons, channels, or raceways. The open pond can have a depth of from about 3 cm to about 500 cm, and will typically have a depth of from about 5 cm to about 100 cm, such as from about 8 cm to about 50 cm, or from about 10 cm to about 40 cm.

Cells can additionally or alternatively be cultured in a photobioreactor equipped with an artificial light source and/or can having one or more walls that is transparent enough to light, including sunlight, to enable, facilitate, and/or maintain acceptable microorganism growth. The photobioreactor includes an enclosure or partial enclosure in which cells are cultured, optionally in suspension and, when suspended, preferably in an aqueous liquid. Photosynthetic microorganisms can be cultured in a photobioreactor where the culture is actively mixed, for example, during at least a portion of the light period, where active mixing is mixing that requires a power source for moving a liquid (e.g., culture media), gas, or physical structure (e.g., paddlewheel) to effect mixing of cells within the culture medium. For example, active mixing can be by means of a one or more propellers, paddles, or blades, by pumps, including mechanical and air lift pumps, by gas spargers (including gas bubbling tubes) or by means of one or more streams or jets of liquid or gas, and can further include one or more stationary structures (passive mixing devices or structures) within the photobioreactor or along one or more of its walls that promotes turbulence to effect mixing within the culture. The photobioreactor can be, as non-limiting examples, a flexible bioreactor (for example, a flexible floating bioreactor, a hanging bag reactor), a tubular bioreactor, a flat plate bioreactor, an airlift bioreactor, a bubble column bioreactor, a cascade bioreactor, or a bioreactor including elements of any of these types, or other types of bioreactors. A photobioreactor can have a light path (corresponding to the width (depth) or diameter of the bioreactor chamber measured from a boundary of the photobioreactor that is exposed to light) of from about 3 cm to about 500 cm, and in some examples can have a depth of from about 5 cm to about 200 cm. A photobioreactor can use natural light (sunlight) as a light source, where the bioreactor includes at least one surface that transmits light. Alternatively or in addition, a bioreactor can include an artificial light source that can be positioned to direct light into the bioreactor (such as through a transparent wall or cover of the bioreactor) or, alternatively, can be positioned within the bioreactor. A bioreactor can in some examples include one or more structures for directing light, for example, sunlight, to the cells within the bioreactor. Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Culturing refers to the intentional fostering of growth (e.g., increases in cell size, cellular contents, and/or cellular activity, e.g., biomolecule synthesis) and/or propagation (e.g., increases in cell numbers via mitosis) of one or more cells by use of selected and/or controlled conditions. The combination of both growth and propagation may be termed proliferation. Non-limiting examples of selected and/or controlled conditions can include the use of a defined medium (with known characteristics such as pH, ionic strength, and/or carbon source), specified temperature, oxygen tension, carbon dioxide levels, growth in a bioreactor, mixing of the culture, or the like, or combinations thereof. In some embodiments, the microorganism can be grown heterotrophically or mixotrophically, using both light and a reduced carbon source. The microorganism can preferably be cultured phototrophically. When growing or propagating phototrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. If an organic carbon molecule or compound is provided in the culture medium of a microorganism grown phototrophically, it generally cannot be taken up and/or metabolized by the cell for energy and/or typically is not present in an amount sufficient to provide sustainable energy for the growth of the cell culture.

A source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pretreat such sources such that the CO level introduced into the (photo)bioreactor do not constitute a dangerous and/or lethal dose vis-à-vis the growth and/or survival of the microorganisms.

The growth medium can be any that supports growth of the photosynthetic microorganism. Non-limiting examples of growth media include those generally available from a wide variety of sources, where instructions for the preparation of particular media suitable for a wide variety of strains of microorganisms can be obtained from textbooks, the scientific literature, culture collections, and websites. For example, various fresh water and salt water media can include those described in Barsanti, L. amd Gualtieri, P. (2005) Algae: Anatomy, Biochemistry, and Biotechnology, CRC Press, Taylor & Francis Group, Boca Raton, Fla., USA, which is incorporated herein by reference for media and methods for culturing algae. Algal media recipes can also be found at the websites of various algal culture collections, including, as nonlimiting examples, the UTEX Culture Collection of Algae (sbs.utexas.edu/utex/media.aspx); Culture Collection of Algae and Protozoa (ccap.ac.uk/media/pdfrecipes); and Katedra Botaniky (/botany.natur.cuni.cz/algo/caup-media.html). Recipes for growth media can be developed or optimized, for example for particular strains or growth conditions. Microorganisms that can be useful in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of lipid and/or hydrocarbon constituents can vary. In some cases, certain strains of microorganisms may be unable to grow in a particular growth medium because of the presence of some inhibitory component or the absence of some essential nutritional requirement required by the particular strain of microorganism.

In some embodiments, a microorganism that produces one or more free fatty acids can be cultured in a medium that includes an increased concentration of a metal (typically provided as a salt and/or in an ionic form) such as, for example, sodium, potassium, magnesium, calcium, iron, or the like, or combinations thereof (particularly multivalent metals, such as magnesium, calcium, and/or iron), with respect to a standard medium formulation, such as, for example, standard BG-11 medium (ATCC Medium 616, Table 2), or a modified medium such as ATCC Medium 854 (BG-11 modified to contain vitamin B12) or ATCC Medium 617 (BG-11 modified for marine cyanobacteria, containing additional NaCl and vitamin B12). For example, a medium used for growing microorganisms that produce and release into the culture medium one or more free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g., calcium) as compared to a standard medium. The medium used for growing microorganisms that can produce free fatty acids can include, for example, at least about 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g., calcium) in the formulation. Addition of metal (e.g., calcium) in the medium can additionally or alternately increase the tolerance of microorganism in media with a relatively high concentration of free fatty acids. Additionally or alternately, fatty acid-producing strains can advantageously be more robust with excess metal (e.g., calcium) content. Other details regarding the use of a soap-forming ion source in the algal medium are described in the co-pending, commonly-assigned U.S. patent application 61/426,602, filed Dec. 23, 2010, and entitled "Culturing a Microorganism in a Medium with an Elevated Level of a Carboxylate Counterion Source", which is incorporated herein by reference.

Culturing of photosynthetic microorganisms can be performed under various conditions, such as under a light/dark cycle, and/or under natural light. In some embodiments, light/dark cycle refers to providing and removing (e.g., switching on and off) the light over a predetermined period, for example, a light dark cycle can be 12 hours of light followed by 12 hours of darkness or 14 hours of light followed by 10 hours of darkness. Alternatively or in addition, the light/dark cycle can be a natural light/dark cycle based on day-length, where the sun is the light source. "Natural light" refers to light not generated artificially, i.e. by lamps, etc., for example, sunlight and reflected sun light. Natural light can optionally be supplemented by artificial light. In some culture systems, the light period of a culture grown under natural light can be extended by the inclusion of one or more artificial light sources.

The methods of the invention include culturing a photosynthetic microorganism in a culture that undergoes mixing, such as active mixing. In general, in a mixed pond or photobioreactor, algae experience a continuous cycle of intermittent light exposure during the light period where the algae spend some of the light period time in the light and some of the light period time in darkness or near-darkness, where the cycle time and the approximate duration times the photosynthetic microorganisms are in light-exposed and dark regions of the pond or bioreactor will depend on the type and speed of mixing, the incident light intensity, the species or strain of algae in the pond, and the culture density. Mixing can be achieved by introducing turbulence into the pond so that the algae continuously rise and fall relative to the surface of the pond (or move toward and away from the light-facing perimeter of the photobioreactor).

Closed photobioreactors typically use combinations of pumps, injectors, and spargers to induce high Reynolds numbers (a measure of turbulence) within the photobioreactor. This results in mixing such that the exposure of algae to incident light (which may be in excess of photosynthetic capacity), is controlled, and prevents extended periods of time when cells are light-limited. By contrast, a conventional open pond typically generates turbulence and potential energy through the lifting action of a paddle wheel (or similar device). Frictional losses resulting from gradual dissipation of the turbulent eddies and circulation currents within the pond can be mitigated by adding one or more additional mixing devices to a pond. Added mixing devices can enhance the turbulence within the pond and facilitate maintaining favorable conditions for capture of incident solar radiation by the algae. Static or passive devices can be used, such as static mixers, cavitation devices, baffles or the like. The passive devices are designed to maintain flow in the pond in the turbulent region over a portion of the pond volume by introducing eddies into the flow. Preferably, the passive devices allow a turbulent flow to be maintained within the pond for as large a pond volume as possible. The passive devices may be incorporated into the floor and/or the walls of the pond structure. Preferably, the passive structures are located underneath the surface of the pond.

Alternatively or in addition, one or more active mixing devices can be included at one or more locations in the pond. For example, high efficiency, slow turning in-water propellers can be added to effect or enhance mixing. A slow turning propeller refers here to propellers that turn slowly enough to mitigate or avoid damage to the algae within the pond. The speed of such device will be dependent on the species of algae and its resistance to lysing by shear forces. These active mixing devices are added to the extent needed to generate a desired amount of turbulence throughout the pond. Such mixing devices can also be employed in a photobioreactor.

The operation of active mixing devices can be optimized in relation to growth and harvesting cycles that occur over a course of a day, or over the algae life cycle. For example, in night time conditions, the additional active mixing devices in a pond or photobioreactor that uses natural light can be shut off. Since there is no incident sunlight, the light intensity experienced by the algae is not affected by the presence or absence of sufficient turbulence. In this situation, a paddle wheel (for a pond) may provide sufficient turbulence in a non-photosynthetic environment. In another example, algae in a pond may go first through a cell division/cell growth stage. A change in nutrients, pH, or another trigger is then be used to cause the algae to enter an oil production/secretion phase. During the first phase, additional in-water propellers are activated to improve the growth rate of the algae. In the second phase for oil production, the water propellers are stopped, resulting in reduced mixing so that oil can float to the surface and separate more easily.

The depth of a pond or light path of a photobioreactor also plays a factor in the amount of mixing that is needed to achieve a desired level of turbulence. For example, the depth of the growth pond can have a substantial impact on the Reynolds number for the pond. As an illustrative example, if the depth of the pond is reduced from 30 cm to 10 cm, the Reynolds number of such a pond can increase from about 1000 to about 3000.

Where the methods of the invention comprise production of a biomolecule, the culture methods can include inducing expression of a gene encoding a polypeptide for the production of the biomolecule. For example, for the production of fatty acids or fatty acid derivatives, the culture methods can include inducing expression of a thioesterase gene, a lipase gene, or another gene for the production of free fatty acids or fatty acid derivatives. Inducing expression can include adding a nutrient or compound to the culture, removing one or more components from the culture medium, increasing or decreasing light and/or temperature, and/or other manipulations that promote expression of the thioesterase, lipase, or other gene. Such manipulations can largely depend on the nature of the (heterologous) promoter operably linked to the thioesterase, lipase (or other) gene.

For production of certain products, such as, but not limited to, lipids such as fatty acids or fatty acid derivatives, photosynthetic microorganisms can additionally or alternately be cultured in shake flasks, test tubes, vials, microtiter dishes, petri dishes, or the like, or combinations thereof, where the cultures are subjected to intermittent light.

Biomass of the microorganism culture can be recovered by harvesting the microorganism from the medium, for example, by filtering, settling, centrifugation, or combinations thereof. In biomass production embodiments according to the invention, the amount of the biomass produced and/or recovered by the method described herein, measured as ash free dry weight (AFDW) can advantageously be at least about 0.05 g per liter of culture, for example at least about 0.1 g, at least about 0.2 g, at least about 0.3 g, at least about 0.4 g, at least about 0.5 g, at least about 0.6 g, at least about 0.7 g per liter of culture, at least about 1 g per liter of culture, at least about 1.5 g per liter of culture, at least about 2 g per liter of culture, at least about 2.5 g per liter of culture, or at least about 5 g per liter of culture. Although many times the goal can be to produce and/or recover as much biomass as possible, in some instances the amount of the biomass produced and/or recovered by the method described herein, measured as ash free dry weigh (AFDW) can be limited to about 15 g or less per liter of culture, for example about 12 g or less per liter of culture, about 10 g or less per liter of culture, about 5 g or less per liter of culture, about 2 g or less per liter of culture, about 1 g or less per liter of culture, or about 0.5 g or less per liter of culture.

Biomass can be used in any of a number of ways, for example, it can be processed for use as a biofuel by generating syngas from the biomass, can be supplied to an anaerobic digester for production of one or more alcohols, or the biomass can be extracted to provide algal lipids, such as but not limited to monoglycerides, diglycerides, or triglycerides, fatty acid alkyl esters, fatty acids, and/or fatty acid derivatives.

In some embodiments, fatty acids and fatty acid derivatives can be recovered from culture by recovery means known to those of ordinary skill in the art, such as by whole culture extraction, for example, using organic solvents. In some cases, recovery of fatty acids or fatty acid derivatives (such as fatty acid esters) can be enhanced by homogenization of the cells, as provided in the examples herein. When fatty acids are sufficiently released from the microorganisms into the culture medium, the recovery method can be adapted to efficiently recover only the released fatty acids, only the fatty acids produced and stored within the microorganisms, or both the produced and released fatty acids.

In further embodiments, products such as but not limited to free fatty acids and fatty acid derivatives that are secreted/released into the culture medium by the recombinant microorganisms described above can be recovered in a variety of ways. A straightforward isolation method, e.g., by partition using immiscible solvents, may be employed. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acids can then be eluted from the particulate adsorbents, e.g., by the use of an appropriate solvent. In such circumstances, one isolation method can include carrying out evaporation of the solvent, followed by further processing of the isolated fatty acids and lipids, to yield chemicals and/or fuels that can be used for a variety of commercial purposes.

The microorganisms according to some embodiments of the present invention produces free fatty acids and fatty acid derivatives in an amount greater than the amount of free fatty acids and fatty acid derivatives produced by a strain having an intact (nondisrupted) NPQ process grown under identical conditions.

Additionally or alternately, the present invention can include one or more of the following embodiments.

Embodiment 1

A method of producing biomass or at least one biomolecule comprising culturing a photosynthetic microorganism that comprises a disrupted Non-Photochemical Quenching (NPQ) process in a pond or bioreactor that includes at least one active mixing device under conditions sufficient for the microorganism to proliferate in the culture, and isolating biomass or at least one biomolecule from the culture.

Embodiment 2

The method of embodiment 1, wherein the amount of biomass or a biomolecule produced by the culture is at least 10% greater, for example at least 15% greater, at least 20% greater, or at least 25% greater, than the amount of biomass or a biomolecule produced by an identical culture of a microorganism identical in all respects except that it does not have a disrupted NPQ process.

Embodiment 3

The method of embodiment 1 or embodiment 2, wherein the culture volume is at least 20 liters, for example at least 50 liters, at least 100 liters, at least 200 liters, or at least 400 liters.

Embodiment 4

The method of any one of the previous embodiments, wherein the photosynthetic microorganism is cultured phototrophically, such as under a light/dark cycle and/or under natural light.

Embodiment 5

The method of any one of the previous embodiments, wherein disrupting the NPQ process comprises disrupting the production of at least one carotenoid (e.g., comprising echinenone and/or hydroxyechinenone) and/or reducing the expression of at least one carotenoid binding protein (e.g., comprising OCP) in the microorganism.

Embodiment 6

The method of embodiment 5, wherein disrupting the NPQ process comprises inhibiting the expression of an OCP in the microorganism, optionally wherein one or more of the following are satisfied: the OCP is mutated to an inactive form, the OCP gene in the microorganism is disrupted by insertional mutagenesis, all or a portion of the OCP gene in the microorganism is removed, the microorganism expresses an antisense molecule that targets the OCP gene, the microorganism expresses a ribozyme that targets the OCP gene.

Embodiment 7

The method of any one of the previous embodiments, wherein the microorganism is a cyanobacterium, such as selected from a group of genera consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Crocosphaera, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema,* and *Xenococcus.*

Embodiment 8

The method of Embodiment 7, wherein the photosynthetic microorganism is a species of *Synechocystis, Arthrospira, Microcystis, Lyngbya, Nostoc, Anabaena, Synechococcus, Gloeobacter, Crocosphaera,* or *Thermosynechococcus.*

Embodiment 9

The method of any of embodiments 5-8, wherein the OCP has at least 40%, at least 45%, at least 50%, for example at least 55%, at least 60%, at least 65%, at least 70%, at least 75%, at least 80%, at least 85%, at least 90%, or at least 95%, identity to SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

Embodiment 10

The method of any one of the previous embodiments, wherein the microorganism produces at least 0.3 g/L of biomass.

Embodiment 11

The method of any one of the previous embodiments, wherein the microorganism produces a free fatty acid (e.g., including at least one $C_{12}$ to $C_{24}$ fatty acid) or a fatty acid derivative (e.g., including at least one fatty acid derivative comprising an acyl chain length from 12 to 24 carbons and/or comprising a fatty aldehyde, a fatty alcohol, a wax ester, an alkene, and/or an alkane).

Embodiment 12

The method of embodiment 11, wherein the amount of free fatty acid or fatty acid derivative produced is greater than the amount of free fatty acid or fatty acid derivative produced by an identical culture of a microorganism identical in all respects except that it does not have a disrupted NPQ process that is grown under identical conditions.

Embodiment 13

The method of embodiment 11 or 12, wherein the microorganism comprises an exogenous nucleic acid molecule encoding a thioesterase (e.g., comprising an acyl-ACP thioesterase, an acyl-CoA thioesterase, a hydroxylbenzoyl-CoA thioesterase, or a combination thereof) and/or lipase (e.g., a member of Pfam PF01674, Pfam PF01764, Pfam PF07819, Pfam PF03583, or Pfam PF00151, such as a member of Pfam PF01674, Pfam PF01764, or Pfam PF07819).

Further additionally or alternately, there can be a method according to any one of the preceding method embodiments, wherein the medium used for culturing the fatty acid-producing organism can include an increased concentration of a soap-forming ion source (e.g., an inorganic soap-forming ion source, a metal ion source, a multivalent metal ion source, a divalent metal ion source, or some combination thereof, such as sodium, potassium, magnesium, calcium, iron, or combinations thereof, particularly multivalent metals, such as magnesium, calcium, and/or iron), with respect to a standard medium formulation (e.g., standard BG-11 medium) or a modified medium (e.g., ATCC Medium 854 or ATCC Medium 617), which increased concentration can optionally be at least about 0.5 mM (e.g., between about 0.5 mM and about 1 mM, between about 1 mM and about 2 mM, between about 2 mM and about 5 mM, between about 5 mM and about 10 mM, between about 10 mM and about 25 mM, and/or greater than 25 mM) and/or can optionally but preferably be at least 2-fold (e.g., at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold) as compared to said standard/modified medium.

Without further description, it is believed that one of ordinary skill in the art can, using the preceding description and the following illustrative examples, make and utilize the present invention and practice the claimed methods. The following working examples, therefore, specifically point out representative embodiments of the present invention, some preferred, and are not to be construed as limiting in any way the remainder of the disclosure.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and/or alterations can be employed without departing from the scope of the presently disclosed subject matter.

Example 1

Absence of NPQ

A puc 19-based construct was designed for interrupting the OCP gene of *Synechocystis* sp. PCC 6803, in which a kanamycin resistance gene was positioned between *Synechocystis* sequences that occur upstream and downstream of the gene encoding Orange Carotenoid Protein in the *Synechocystis* genome (FIG. 1). The sequences of the construct is provided as SEQ ID NO:3. The construct was designed such that recombination of the [OCP upstream sequences—kanamycin resistance gene—OCP downstream sequences] into the *Syn-* echocystis genome results in replacement of the OCP gene with the kanamycin resistances gene. Thus, kanamycin resistant transformants lack an OCP gene.

The construct having the knock-out gene integration organization as provided in FIG. 1 was transformed into *Synechocystis* using standard transformation methods essentially as disclosed in Zang et al. (2007) *J. Microbiol.* 45: 241-245, and kanamycin resistant colonies were grown up and tested for the absence of the OCP gene and the presence of the kanamycin gene in separate PCR assays. One confirmed knockout isolate, designated ΔOCP, was used for further study.

Chlorophyll fluorometry was used to verify that the OCP knockout strain was deficient in blue light induced NPQ, the established function of the OCP (Wilson et al. (2006) *The Plant Cell* 18: 992-1007; Boulay et al. (2008) *Biochimica et Biophysica Acta* 1777: 1344-1354).

Fluorescence after stimulation with blue light was determined using a Walz Dual-PAM-100 fluorometer according to established methods (see, for example, Wilson et al. (2006); Boulay et al. (2008)). To prepare the cells, cell cultures of ΔOCP and wild type were grown in ~100 mL shake flasks under ~50 microEinsteins (μE) of light in the presence of ~1% $CO_2$ in BG-11 medium. A ~10 mL aliquot of each culture was removed, spun down at ~4,000 rpm for about 3 mins, and resuspended in ~2 mL of water, and the cells were dark-acclimated for about one hour prior to transferring to cuvettes for taking fluorescence measurements. The measuring light was turned on for ~1 minute prior to exposing the cells to saturation flashes of ~10,000 E for measuring Fv/Fm. The samples were then exposed to saturating flashes (spikes) of blue light at ~400 E (start of exposure to blue light marked by an asterisks on the graphs of FIGS. 2A and 2B; blue light turned off marked by squares). The dark recovery of Fv/Fm was followed by the occasional application of saturating blue light flashes.

Figure 2:
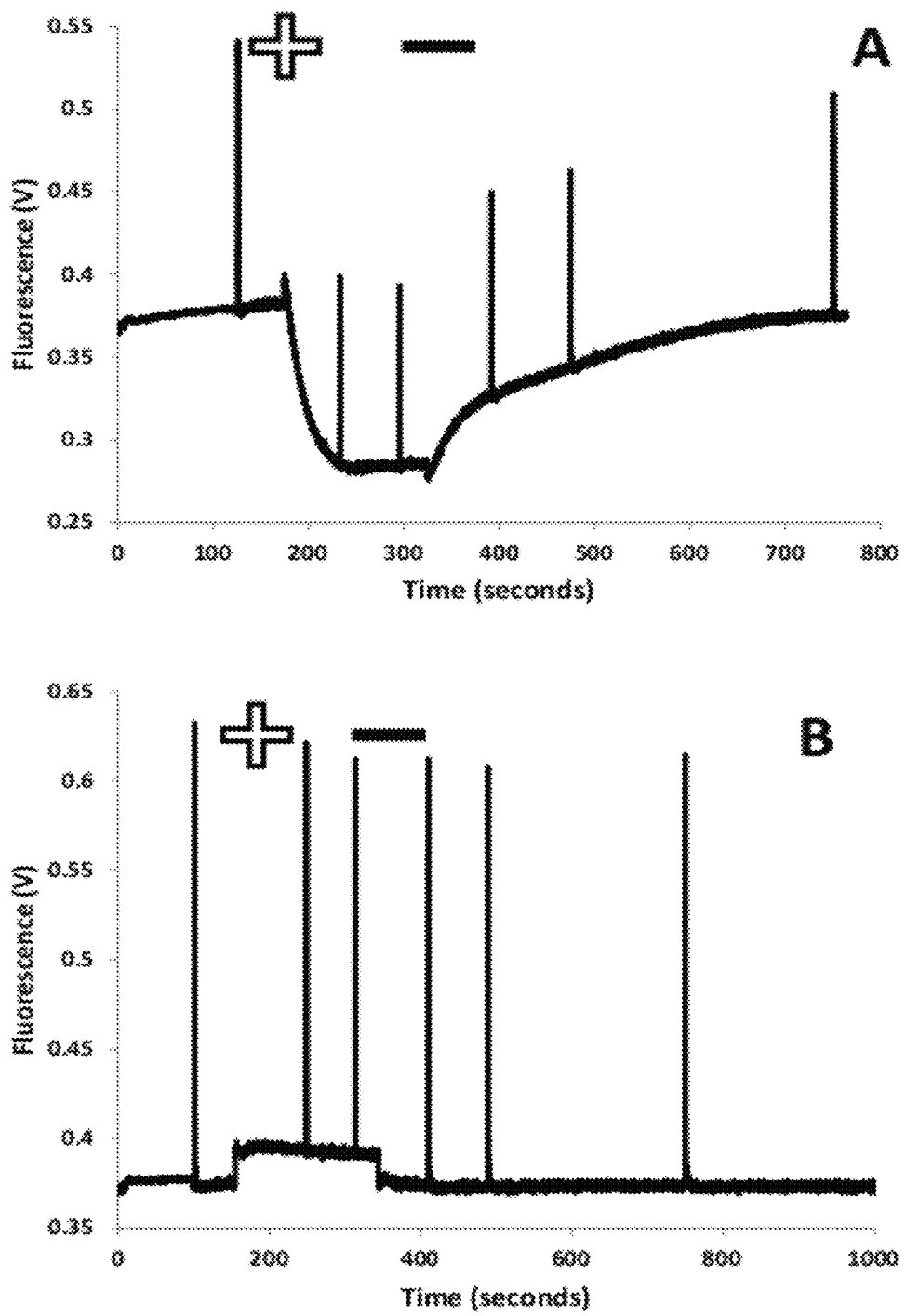
FIG. 2 graphically shows the output of Chlorophyll-a Pulse Amplitude Modulated Fluorometry on *Synechocystis* PCC6803, showing that the application of high blue light (+) induces NPQ in WT (A) but not in ΔOCP(B) NQP can be determined by the reduction in fluorescence yield of a saturating flash of light (shown as spikes). A lower spike after the + indicates higher NPQ.

FIG. 2A shows the fluorescence traces of wild type cells. The chlorophyll fluorescence was quenched when samples were shifted from dark to blue light (shown by a plus sign). The quenching was induced faster than it relaxed after a shift back to dark (shown by a minus sign). The wild-type (WT) had an OCP, while the strain without an OCP (ΔOCP) shows no blue light induction of NPQ, as seen in FIG. 2B.

FIG. 2A also shows that NPQ was slow to relax in comparison to the time it took for induction.

Example 2

Production of Biomass

To investigate biomass accumulation, *Synechocystis* was grown in either controlled laboratory environments or in a greenhouse with natural light. Cell biomass was estimated using the standard ash-free dry weight method. Ash-free dry weights (a measurement of the weight of organic material in algal cultures) were determined by removing water from a sample of the growth culture, drying the sample, recording the weight, combusting the sample, and recording the weight of the remaining residue.

In the greenhouse growth experiments, cultures of *Synechocystis* sp. PCC 6803 wild type and *Synechocystis* sp. PCC 6803 Deleted Orange Carotenoid Protein strains were inoculated into ~150 mls of BG-11 media. After each ~24 hour period of greenhouse growth, the culture was brought up to a total volume of ~150 mls with distilled water to make up for any evaporation, and then half of the culture was removed and replaced with BG-11 media. About 25-35 mls of the harvested sample was assessed for ash-free dry weight (AFDW) by filtering the cells, drying the biomass in an oven, recording the weight of the dried biomass, combusting the dried sample in a furnace, and weighing the remaining residue after combusting. The dry weight (DW) and ash-free dry weight (AFDW) were calculated according to the formulas:

$$DW(g/l) = \frac{(ovenweight(g) - filterweight(g)) * 1000(ml/l)}{samplevolume(ml)}$$

$$AFDW(g/l) = DW(g/l) - \left(\frac{(furnaceweight(g) - filterweight(g))}{samplevolume(ml)} * 1000(ml/l)\right)$$

Where "ovenweight" is the weight of the sample after drying in the oven, and "furnaceweight" is the weight of the same sample after combusting in the muffle furnace.

Briefly, ~25 mls, ~30 mls, or ~35 mls of removed sample of each culture was transferred to a filtration assembly that included a side arm flask fitted with a stopper, funnel, and screen for supporting a filter held with a clamp. A pre-weighed Whatman 47 mm GF/F glass microfiber filter was positioned over the screen. The sample was pipetted onto the surface of the filter, and a vacuum (about 5-10 psi) was applied via the side arm of the flask. Once all the liquid passed through the filter, the sides of the funnel were rinsed with ~9-12 mls of distilled water to bring down any cells that may have stuck to the side of the funnel. The rinsing step was repeated twice. The clamp was removed to disassemble the filtration unit, and the filter was removed from the base with forceps. The filter was placed in a pre-weighed aluminum weighing boat, and then the samples were placed in a ~105° C. drying oven until the weight was constant, at least four hours. The dried samples were then place in a dessicator to cool, and then the weigh boat plus filter was weighed. Dry weight was calculated as:

$$DW(g/l) = \frac{(ovenweight(g) - vialweight(g)) * 1000(ml/l)}{samplevolume(ml)}$$

Samples were then place into a muffle furnace heated to ~550° C. for ~1 hour. The samples were then removed using tongs and transferred to the desiccator to cool to room temperature. When the samples were cool, they were weighed using the same analytical balance used to weigh the dry samples.

Ash Free Dry Weight (in g/l) was calculated as follows:

$$AFDW(g/l) = DW(g/l) - \left(\frac{(furnaceweight(g) - vialweight(g))}{samplevolume(ml)} * 1000(ml/l)\right)$$

The Ash Free Dry Weight of the culture was then calculated based on the culture volume.

In the laboratory the cells were grown in 250 ml tissue culture flasks and bubbled vigorously with air. Cells were grown at ~30° C., and light was supplied by white LEDs that were programmed according to: ~16 hours light; ~8 hours dark. Light was ~50 μE background with ~2000 μE flashes supplied every ~2 minutes. The length of the flash was randomized to vary between 10 seconds and 1 minute. Cells were diluted by about one half every day, and culture was harvested for ash-free dry weight. Over ~3 days in these conditions the wild-type culture produced ~0.09 grams per liter of the culture. The ΔOCP mutant produced ~0.12 grams of biomass per liter.

In the greenhouse, samples were: incubated to an equal optical density {OD at ~720 nm). The cultures were bubbled with air in ~250 ml tissue flasks that were submerged in a ~300° C. water bath. To approximate the light environment of a dense production system, the bottom ~⅓ of the flask was made to be opaque, with only approximately 25% of the total culture volume exposed to full sunlight. Cell growth and ash-free dry weights were followed for several days in these conditions.

Figure 3:
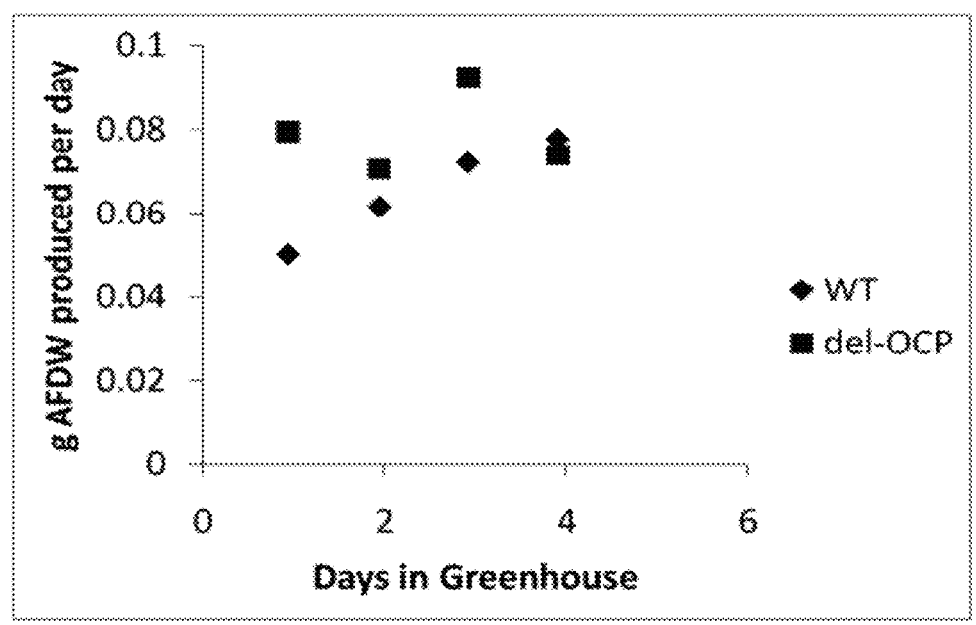
FIG. 3 shows daily biomass production of *Synechocystis* cultures grown over 4 days.

On day 0 cells were inoculated in flasks in the greenhouse. One day later, about one half of the culture was removed and replaced with an equal volume of fresh media. The removed cells were spun down and analyzed for ash-free dry weight. The same procedure was repeated on days 1, 2, 3, and 4. The accumulative biomass produced by the culture is shown in Table 1, and the daily biomass produced by the culture is shown in FIG. 3.

TABLE 1

Accumulative biomass produced by WT and OCP knock-out (ΔOCP)

|  | Biomass produced by WT (g/liter) | Biomass produced by ΔOCP (g/liter) |
| --- | --- | --- |
| Day 1 | 0.05 | 0.08 |
| Day 2 | 0.11 | 0.15 |
| Day 3 | 0.18 | 0.24 |
| Day 4 | 0.26 | 0.32 |

The results of the biomass accumulation experiment demonstrate that eliminating OCP and decreasing NPQ (as shown in Example 1) did not result have a deleterious effect on biomass accumulation as might be expected if excessive photodamage occurred. In fact, as shown in FIG. 3, cells having a disrupted NPQ process due to knock out of the OCP gene accumulated approximately 28% more biomass than wild type ("non OCP-knock-out") cells, suggesting that reduction of NPQ allowed a higher proportion of photons to provide energy for photochemistry and biochemical pathways that generate biomass.

What is claimed is:

1. A method of producing biomass or at least one free fatty acid or fatty acid derivative, the method comprising:
    culturing a cyanobacterium that comprises a disrupted Non-Photochemical Quenching (NPQ) process in a suitable culture medium as an actively mixed culture in a pond or bioreactor that includes at least one active mixing device, wherein the cyanobacterium experiences intermittent light conditions as a result of movement between brighter and darker regions of the pond or bioreactor, and wherein the NPQ process is disrupted by attenuating or eliminating production of at least one carotenoid by disrupting a gene encoding β-carotene hydroxylase (CrtR), disrupting a gene encoding a β-carotene monoketolase (CrtO), and/or disrupting a gene encoding orange carotenoid protein (OCP), and further wherein disruption of the NPQ process does not include attenuating the expression of a light harvesting chlorophyll binding protein, and
    isolating biomass or at least one free fatty acid or fatty acid derivative from the actively mixed culture, wherein the amount of biomass or the amount of at least one free fatty acid or fatty acid derivative produced by the actively mixed culture is at least 20% greater than the amount of biomass or the amount of at least one free fatty acid or fatty acid derivative produced by a control culture, wherein the control culture is identical to the actively mixed culture in all material respects except that the control culture cyanobacterium does not have a disrupted NPQ process.

2. The method of claim 1, wherein the cyanobacterium is cultured under natural light.

3. The method of claim 1, wherein the at least one carotenoid comprises echinenone and/or hydroxyechinenone.

4. The method of claim 1, wherein disrupting the NPQ process comprises disrupting the OCP gene in the cyanobacterium.

5. The method of claim 4, wherein the OCP gene is disrupted by removing all or a portion of the OCP gene in the cyanobacterium.

6. The method of claim 1, wherein the cyanobacterium is selected from a group of genera consisting of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Crocosphaera, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Micro coleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermocynechococus, Tolypothrix, Trichodesmium, Tychonema*, and *Xenococcus*.

7. The method of claim 1, wherein the cyanobacterium produces at least 0.3 g/L of biomass.

8. The method of claim 1, wherein the cyanobacterium comprises at least one non-native nucleic acid molecule encoding a thioesterase or a polypeptide having lipolytic activity.

9. The method of claim 8, wherein the cyanobacterium produces a free fatty acid or a fatty acid derivative.

10. The method of claim 9, wherein the amount of free fatty acid or fatty acid derivative produced is greater than the amount of free fatty acid or fatty acid derivative produced by the control culture.

11. The method of claim 9, wherein the free fatty acid produced includes at least one $C_{12}$ to $C_{24}$ free fatty acid.

12. The method of claim 9, wherein the fatty acid derivative produced includes at least one fatty acid derivative comprising an acyl chain length from 12 to 24 carbons.

13. The method of claim 1, wherein the OCP gene is disrupted by homologous recombination.

14. A method of producing biomass or at least one free fatty acid or fatty acid derivative, the method comprising:
    culturing a cyanobacterium that comprises a disrupted NPQ process in a suitable culture medium as an actively mixed culture in a pond or bioreactor that includes at least one active mixing device, wherein the cyanobacterium experiences intermittent light conditions as a result of movement between brighter and darker regions of the pond or bioreactor, and wherein the NPQ process is disrupted by a means for disrupting production of at least one carotenoid and/or a means for reducing expression of at least one carotenoid binding protein, and further wherein disruption of the NPQ process does not include attenuating the expression of a light harvesting chlorophyll binding protein; and isolating biomass or at least one free fatty acid or fatty acid derivative from the actively mixed culture, wherein the amount of biomass or the amount of at least one free fatty acid or fatty acid derivative produced by the actively mixed culture is at least 20% greater than the amount of biomass or the amount of at least one free fatty acid or fatty acid derivative produced by a control culture, wherein the control culture is identical to the actively mixed culture in all material respects except that the control culture cyanobacterium does not have a disrupted NPQ process.

15. The method of claim 14, wherein the means for disrupting production of at least one carotenoid targets a crtO gene or a crtR gene, and/or wherein the means for reducing expression of at least one carotenoid binding protein targets an ocp gene.

16. The method of claim 14, wherein the means for disrupting production of at least one carotenoid and/or wherein the means for reducing expression of at least one carotenoid binding protein is homologous recombination.

17. The method of claim 16, wherein the means for disrupting production of at least one carotenoid targets a crtO gene or a crtR gene, and/or wherein the means for reducing expression of at least one carotenoid binding protein targets an ocp gene.

* * * * *